(12) United States Patent
Yadav et al.

(10) Patent No.: US 8,870,787 B2
(45) Date of Patent: Oct. 28, 2014

(54) VENTRICULAR SHUNT SYSTEM AND METHOD

(75) Inventors: Jay Yadav, Atlanta, GA (US); Florent Cros, Decatur, GA (US)

(73) Assignee: CardioMEMS, Inc., Atlanta, GA (US)

( * ) Notice: Subject to any disclaimer, the term of this patent is extended or adjusted under 35 U.S.C. 154(b) by 1036 days.

(21) Appl. No.: 12/509,053

(22) Filed: Jul. 24, 2009

(65) Prior Publication Data

US 2010/0022896 A1  Jan. 28, 2010

Related U.S. Application Data

(60) Continuation-in-part of application No. 12/349,606, filed on Jan. 7, 2009, now Pat. No. 7,679,355, which is (Continued)

(51) Int. Cl.
| | |
|---|---|
| A61B 5/00 | (2006.01) |
| A61B 5/03 | (2006.01) |
| G01R 23/12 | (2006.01) |
| G01R 23/14 | (2006.01) |
| H01Q 7/00 | (2006.01) |
| A61B 5/05 | (2006.01) |
| G01F 15/06 | (2006.01) |
| A61M 27/00 | (2006.01) |
| A61B 5/07 | (2006.01) |

(52) U.S. Cl.
CPC ....... *G01F 15/066* (2013.01); *A61B 2560/0223* (2013.01); *A61B 5/031* (2013.01); *A61M 27/006* (2013.01); *G01R 23/12* (2013.01); *A61B 5/6846* (2013.01); *G01R 23/145* (2013.01); *H01Q 7/00* (2013.01); *A61B 2560/0219* (2013.01); *A61B 5/05* (2013.01); *A61B 5/0031* (2013.01); *A61B 5/076* (2013.01)
USPC .......................................................... 600/561

(58) Field of Classification Search
USPC ................................................. 600/486, 561
See application file for complete search history.

(56) References Cited

U.S. PATENT DOCUMENTS

| 3,350,944 A | 11/1967 | De Michele |
| 3,958,558 A | 5/1976 | Dunphy et al. |

(Continued)

FOREIGN PATENT DOCUMENTS

| AU | 2004274005 A1 | 3/2005 |
| AU | 2009201749 A1 | 5/2009 |

(Continued)

OTHER PUBLICATIONS

International Search Report and Written Opinion for International Application No. PCT/US2010/033396 (mailed Jan. 7, 2011).

(Continued)

*Primary Examiner* — Michael Kahelin
*Assistant Examiner* — Karen Toth
(74) *Attorney, Agent, or Firm* — Ballard Spahr LLP

(57) ABSTRACT

A ventricular shunt systems and methods of preventing hydrocephalus are described herein. In one aspect, the ventricular shunt system has at least one pressure sensor that is configured to be selectively electromagnetically coupled to an ex-vivo source of RF energy and is variable in response to the pressure in a patient's ventricle.

41 Claims, 22 Drawing Sheets

Related U.S. Application Data a division of application No. 11/276,571, filed on Mar. 6, 2006, now Pat. No. 7,498,799, which is a continuation-in-part of application No. 11/105,294, filed on Apr. 13, 2005, now Pat. No. 7,245,117, application No. 12/509,053, which is a continuation-in-part of application No. 11/613,645, filed on Dec. 20, 2006, now Pat. No. 7,550,978, which is a continuation of application No. 11/105,294, filed on Apr. 13, 2005, now Pat. No. 7,245,117, application No. 12/509,053, which is a continuation-in-part of application No. 12/175,803, filed on Jul. 18, 2008, which is a division of application No. 11/472,905, filed on Jun. 22, 2006, now Pat. No. 7,574,792, which is a division of application No. 10/943,772, filed on Sep. 16, 2004, now abandoned, application No. 12/509,053, which is a continuation-in-part of application No. 11/157,375, filed on Jun. 21, 2005.

(60) Provisional application No. 60/623,959, filed on Nov. 1, 2004, provisional application No. 60/658,680, filed on Mar. 4, 2005, provisional application No. 60/623,959, filed on Nov. 1, 2004, provisional application No. 60/503,745, filed on Sep. 16, 2003.

(56) References Cited

U.S. PATENT DOCUMENTS

| | | | |
|---|---|---|---|
| 4,026,276 A * | 5/1977 | Chubbuck | 600/407 |
| 4,114,606 A | 9/1978 | Seylar | |
| 4,127,110 A | 11/1978 | Bullara | |
| 4,206,762 A | 6/1980 | Cosman | |
| 4,378,809 A | 4/1983 | Cosman | |
| 4,385,636 A * | 5/1983 | Cosman | 600/561 |
| 4,593,703 A | 6/1986 | Cosman | |
| 4,660,568 A | 4/1987 | Cosman | |
| 4,815,472 A * | 3/1989 | Wise et al. | 600/488 |
| 4,846,191 A | 7/1989 | Brockway et al. | |
| 5,535,752 A | 7/1996 | Halperin et al. | |
| 5,722,414 A | 3/1998 | Archibald et al. | |
| 6,033,366 A | 3/2000 | Brockway et al. | |
| 6,053,873 A | 4/2000 | Govari et al. | |
| 6,113,553 A | 9/2000 | Chubbuck | |
| 6,206,835 B1 | 3/2001 | Spillman, Jr. et al. | |
| 6,237,398 B1 | 5/2001 | Porat et al. | |
| 6,248,080 B1 * | 6/2001 | Miesel et al. | 600/561 |
| 6,277,078 B1 | 8/2001 | Porat et al. | |
| 6,409,674 B1 | 6/2002 | Brockway et al. | |
| 6,416,474 B1 | 7/2002 | Penner et al. | |
| 6,442,413 B1 | 8/2002 | Silver | |
| 6,454,720 B1 | 9/2002 | Clerc et al. | |
| 6,533,733 B1 * | 3/2003 | Ericson et al. | 600/561 |
| 6,577,893 B1 | 6/2003 | Besson et al. | |
| 6,749,574 B2 | 6/2004 | O'Keefe | |
| 6,837,438 B1 | 1/2005 | Takasugi et al. | |
| 6,890,300 B2 | 5/2005 | Lloyd et al. | |
| 6,939,299 B1 | 9/2005 | Petersen et al. | |
| 6,943,688 B2 | 9/2005 | Chung et al. | |
| 7,152,477 B2 | 12/2006 | Banholzer et al. | |
| 7,309,330 B2 | 12/2007 | Bertrand et al. | |
| 7,621,878 B2 | 11/2009 | Ericson et al. | |
| 2002/0052563 A1 | 5/2002 | Penn et al. | |
| 2002/0087059 A1 * | 7/2002 | O'keefe | 600/378 |
| 2003/0105388 A1 * | 6/2003 | Roy et al. | 600/300 |
| 2004/0181206 A1 | 9/2004 | Chiu et al. | |
| 2005/0043670 A1 | 2/2005 | Rosenberg | |
| 2005/0075697 A1 | 4/2005 | Olson et al. | |
| 2005/0187482 A1 | 8/2005 | O'Brien et al. | |
| 2006/0025704 A1 | 2/2006 | Stendel et al. | |
| 2006/0052737 A1 | 3/2006 | Bertrand et al. | |
| 2007/0049845 A1 | 3/2007 | Fleischman et al. | |
| 2007/0276294 A1 | 11/2007 | Gupta et al. | |
| 2008/0077016 A1 | 3/2008 | Sparks et al. | |
| 2009/0030397 A1 * | 1/2009 | Stofer et al. | 604/500 |
| 2009/0278553 A1 | 11/2009 | Kroh et al. | |
| 2010/0022896 A1 | 1/2010 | Yadav et al. | |

FOREIGN PATENT DOCUMENTS

| | | |
|---|---|---|
| AU | 2009201750 A1 | 5/2009 |
| AU | 2013263860 A1 | 1/2014 |
| CA | 2539261 A1 | 3/2005 |
| EP | 1491137 A2 | 12/2004 |
| EP | 1677852 A2 | 7/2006 |
| EP | 2090330 A1 | 8/2009 |
| WO | WO-2005/027998 A2 | 3/2005 |
| WO | 2007030489 A1 | 3/2007 |
| WO | WO-2011/011104 A1 | 1/2011 |

OTHER PUBLICATIONS

Supplemental European Search Report and the European Search Opinion for European Application No. 10802580.0 (National Phase of PCT/US/2010/033396) (dated Apr. 29, 2013).

U.S. Appl. No. 13/850,022, Yadav.

Allen, "Micromachined endovascularly implantable wireless aneurysm pressue sensors," International Conference on Solid State Sensors, Actuators and Microsystems, No. 13, pp. 275-278 (2005).

Baum, R.A., et al. "Aneurysm sac pressure measurements after endovascular repair of abdominal aortic aneurysms," The Journal of Vascular Surgery (Jan. 2001).

Chirlian, "Basic network theory," McGraw Hill Book Co., Impendance section: pp. 275-283, 350-355 (1969).

Manwaring ML, et al. "Remote monitoring of intercranial pressure," Institute of Concology; annals of the Academy of Studencia 4, 2001, pp. 77-80.

International Search Report and Written Opinion issued Jan. 7, 2011 for International Patent Application No. PCT/US2010/033396, which was filed on May 3, 2010 and published as WO 2011/011104 on Jan. 27, 2011 (Inventor—Yadev; Applicant—CardioMEMS) (pp. 1-7).

International Preliminary Report on Patentability issued Jan. 24, 2012 for International Patent Application No. PCT/US2010/033396, which was filed on May 3, 2010 and published as WO 2011/011104 on Jan. 27, 2011 (Inventor—Yadev; Applicant—CardioMEMS) (pp. 1-5).

Preliminary Amendment filed Nov. 4, 2009 for U.S. Appl. No. 12/612,070, filed Nov. 4, 2009 and published as U.S. 2010/0058583 on Mar. 11, 2010 (Inventor—Cros; Applicant—CardioMEMS) (pp. 1-3).

Restriction Requirement issued Dec. 9, 2010 for U.S. Appl. No. 12/612,070, filed Nov. 4, 2009 and published as U.S. 2010/0058583 on Mar. 11, 2010 (Inventor—Cros; Applicant—CardioMEMS) (pp. 1-6).

Preliminary Amendment and Response to Restriction Requirement filed Jun. 9, 2011 for U.S. Appl. No. 12/612,070, filed Nov. 4, 2009 and published as U.S. 2010/0058583 on Mar. 11, 2010 (Inventor—Cros; Applicant—CardioMEMS) (pp. 1-4).

Non-Final Office Action issued Aug. 26, 2011 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).

Response to Non-Final Office Action filed Jan. 31, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-13).

Response to Final Office Action filed Jun. 26, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).

Non-Final Office Action issued Jul. 18, 2013 for U.S. Appl. No. 12/612,070, filed Nov. 4, 2009 and published as U.S. 2010/0058583 on Mar. 11, 2010 (Inventor—Cros; Applicant—CardioMEMS) (pp. 1-7).

Amendment and Response to Non-Final Office Action filed Jan. 2, 2014 for U.S. Appl. No. 12/612,070, filed Nov. 4, 2009 and published as U.S. 2010/0058583 on Mar. 11, 2010 (Inventor—Cros; Applicant—CardioMEMS) (pp. 1-9).

(56) References Cited

OTHER PUBLICATIONS

Non-Final Office Action issued Feb. 24, 2014 for U.S. Appl. No. 12/612,070, filed Nov. 4, 2009 and published as U.S. 2010/0058583 on Mar. 11, 2010 (Inventor—Cros; Applicant—CardioMEMS) (pp. 1-10).
Restriction Requirement issued Jan. 15, 2008 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-7).
Response to Restriction Requirement filed Feb. 15, 2008 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-5).
Restriction Requirement issued Apr. 11, 2008 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-7).
Response to Restriction Requirement filed May 12, 2008 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-5).
Non-Final Office Action issued Jun. 12, 2008 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-7).
Response to Non-Final Office Action filed Dec. 12, 2008 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-15).
Examiner Interview Summary issued Apr. 16, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-2).
Notice of Allowance issued Jul. 10, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-4).
Notice of Allowance issued Sep. 29, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-2).
Examiner Interview Summary issued Oct. 30, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-3).
Issue Notification issued Nov. 24, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-1).
Preliminary Amendment filed Jun. 21, 2006 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-8).
Non-Final Office Action issued Oct. 29, 2007 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-12).
Response to Non-Final Office Action filed Jan. 29, 2008 for for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-24).
Supplemental Response to Non-Final Office Action filed May 30, 2008 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-19).
Restriction Requirement issued Aug. 22, 2008 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-6).
Final Office Action issued Aug. 25, 2008 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-12).
Response and Amendment to Final Office Action filed Feb. 25, 2009 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-14).
Non-Final Office Action issued Jun. 1, 2009 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Amendment and Response to Non-Final Office Action filed Oct. 23, 2009 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Final Office Action issued Jul. 29, 2010 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-12).
Amendment in Response to Final Office Action filed Jan. 31, 2011 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Non-Final Office Action issued Jan. 16, 2014 for U.S. Appl. No. 11/157,375, filed Jun. 21, 2005 and published as U.S. 2006/0287602 on Dec. 21, 2006 (Inventor—O'Brien; Applicant—CardioMEMS) (pp. 1-11).
Preliminary Amendment issued Jul. 18, 2008 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-26).
Restriction Requirement issued Sep. 27, 2011 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-26).
Response to Restriction Requirement filed Dec. 14, 2011 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-3).
Non-Final Office Action issued Dec. 20, 2011 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-12).
Response to Non-Final Office Action filed May 29, 2012 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-23).
Final Office Action issued Jul. 13, 2012 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-12).
Response to Final Office Action filed Oct. 13, 2012 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-11).
Non-Final Office Action issued Apr. 15, 2014 for U.S. Appl. No. 12/175,803, filed Jul. 18, 2008 and published as U.S. 2009/0030291 on Jan. 29, 2009 (Inventor—O'Brien; Applicant—CardioMEMS) (pp. 1-14).
Final Office Action issued Mar. 26, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).
Notice of Allowance issued Mar. 23, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-7).
Requirement for Restriction issued Dec. 12, 2006 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-7).

(56) References Cited

OTHER PUBLICATIONS

Response to Restriction Requirement filed Jan. 10, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-5).
Notice of Allowance issued Feb. 14, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Request for Continued Examination filed May 14, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-1).
Notice of Allowance issued Jun. 18, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-2).
Examiner Interview Summary issued Jul. 23, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-2).
Notice of Allowance issued Jul. 23, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Request for Continued Examination filed Oct. 23, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-1).
Notice of Allowance issued Nov. 21, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Request for Continued Examination filed Feb. 21, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Notice of Allowance issued Mar. 5, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-6).
Request for Continued Examination filed Jun. 5, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Notice of Allowance issued Jun. 13, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-6).
Request for Continued Examination filed Sep. 10, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Notice of Allowance issued Oct. 7, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-6).
Issue Notification issued Feb. 11, 2009 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-1).

\* cited by examiner

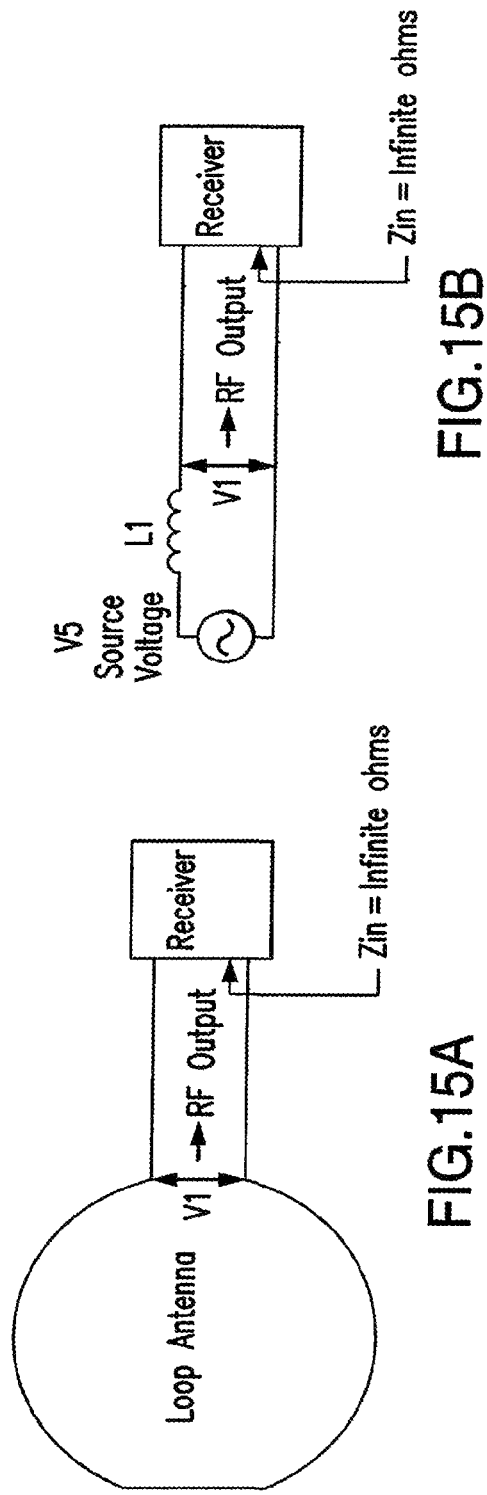

VENTRICULAR SHUNT SYSTEM AND METHOD

This application is a continuation-in-part of pending U.S. patent application Ser. No. 12/349,606, filed on Mar. 6, 2006, which is a divisional patent application of U.S. patent application Ser. No. 11/276,571, filed on Mar. 6, 2006, now issued as U.S. Pat. No. 7,498,799, which is a continuation-in-part of U.S. patent application Ser. No. 11/105,294, filed Apr. 13, 2005 now issued as U.S. Pat. No. 7,245,117, which claims priority to U.S. Provisional Application Ser. No. 60/623,959, filed on Nov. 1, 2004, all of which are incorporated herein by reference. U.S. application Ser. No. 11/276,571 also claims priority to U.S. Provisional Application Ser. No. 60/658,680, filed Mar. 4, 2005, which is also incorporated herein by reference. This application is also a continuation-in-part of pending U.S. patent application Ser. No. 11/613,645, filed on Dec. 20, 2006, which is a continuation of U.S. patent application Ser. No. 11/105,294, filed on Apr. 13, 2005, now U.S. Pat. No. 7,245,117, which claims priority to U.S. Provisional Application No. 60/623,959, filed on Nov. 1, 2004. Further, this application is a continuation-in-part of pending U.S. patent application Ser. No. 12/175,803, filed on Jul. 18, 2008, which is a divisional of pending U.S. patent application Ser. No. 11/472,905, filed on Jun. 22, 2006, which is a divisional of U.S. patent application Ser. No. 10/943,772, filed on Sep. 16, 2004, which claims priority to U.S. Provisional Application No. 60/503,745, filed on Sep. 16, 2003. Additionally, this application is a continuation-in-part of pending U.S. patent application Ser. No. 11/157,375, filed on Jun. 21, 2005.

BACKGROUND OF THE INVENTION

1. Field of the Invention

This invention relates generally to ventricular shunt systems and methods of preventing hydrocephalus, and more particularly to selectively monitoring pressure within at least a portion of a ventricular shunt.

2. Background Art

Hydrocephalus is a condition in which abnormal accumulation of cerebrospinal fluid (CSF) in ventricles of a brain results in increased intracranial pressure, which can result in abnormal enlargement of the head, mental retardation and convulsion. Conventional treatment of hydrocephalus typically requires the surgical insertion of a ventricular shunt into the cerebral ventricles to bypass any obstruction and to place the cerebral ventricles into fluid communication with body cavities in which the CSF can be absorbed by the body, e.g., the pleural cavity, the right atrium, the gallbladder, the peritoneal cavity, and the like.

Conventional ventricular shunts are susceptible to malfunction, typically due to failure and/or infection of the shunt by a bacteria or fungus, which can result in an undesired re-accumulation of CSF in the ventricles of the subject's brain. A ventricular shunt may also stop functioning if it becomes disconnected, blocked, or it is outgrown. The failure rate of shunts is relatively high and it is not uncommon for a patient to require multiple shunt revisions within their lifetime. Furthermore, ventricular shunt failure or malfunction often has a gradual onset that can allow for damage to the patient to occur before the onset of adverse physical symptoms that are sufficiently gross to allow for non-monitored diagnosis.

A conventional ventricular shunt comprises a ventricular catheter, a valve configured to regulate fluid flow and a drainage catheter. In operation, the ventricular catheter is placed within the brain and is connected to the valve. The valve is also connected to the drainage catheter, which is typically placed in fluid communication with a selected body cavity of the patient for resorption. Currently available shunt types included fixed pressure valves, valves with over-drainage protection, and magnetic valves in which pressure can be regulated post-surgery with the use of strong magnets.

There is an unmet need for ventricular shunt systems and methods that are adapted to control and regulate shunt performance and to diagnose onset of shunt malfunction or failure prior to an adverse medical event.

SUMMARY

The application relates to a ventricular shunt system that includes at least one pressure sensor in fluid communication with a ventricle of a patient. It is contemplated that the pressure sensor can be attached to a power source (positioned either external to the patient or within the patient) via conventional wire leads. Optionally, the pressure sensor can be wirelessly configured such that it requires no direct, physical connection to a power source.

In one aspect, the at least one pressure sensor can be mountable thereon a portion of the ventricular shunt system. In another aspect, the at least one pressure sensor can comprise a passive electrical resonant circuit that is configured to be selectively electromagnetically coupled to an ex-vivo source of RF energy. In this aspect, each pressure sensor, in response to the electromagnetic coupling, can be configured to generate an output signal characterized by a frequency that is dependent upon urged movement of a portion of the passive electrical resonant circuit and is indicative of pressure applied thereon a portion of the respective at least one pressure sensor. In one aspect, it is contemplated that the passive electrical resonant circuit of the at least one pressure sensor comprises a LC resonant circuit.

In one operational aspect, the at least one pressure sensor can be positioned in fluid communication with the fluid therein the ventricle of the patient. In this aspect, upon application of a moment or force thereon the at least one pressure sensor, at least a portion of the passive electrical resonant circuit of the at least one pressure sensor can be forced or otherwise urged to move with a resultant change in the resonant frequency of the at least one pressure sensor when it is energized via the electromagnetic coupling. The sensed frequency of the at least one pressure sensor is indicative of the fluid pressure therein the ventricle of the patient.

In a further operational aspect, the at least one pressure sensor can be positioned in communication with a fluid filled reservoir that is positioned therein a portion of the ventricle of the patient. In this aspect, the fluid filled reservoir can be mountable adjacent a ventricular catheter that is in fluid communication with the ventricle of the patient. In this aspect, application of a force thereon the surface of the fluid filled chamber causes a like force to be exerted thereon the at least one pressure sensor, which results in at least a portion of the passive electrical resonant circuit of the at least one pressure sensor to be forced or otherwise urged to move with a resultant change in the resonant frequency of the at least one pressure sensor when it is energized via the electromagnetic coupling. The sensed frequency of the at least one pressure sensor is indicative of the fluid pressure therein the ventricle of the patient.

BRIEF DESCRIPTION OF THE DRAWINGS

These and other features of the preferred embodiments of the invention will become more apparent in the detailed description in which reference is made to the appended drawings wherein:

FIG. 15A illustrates a loop terminated into a receiver with a high input impedance and FIG. 15B illustrates its equivalent circuit.

FIGS. 19(*b*), 19(*c*) and 19(*d*) are graphs illustrating exemplary coupled signals.

DETAILED DESCRIPTION OF THE INVENTION

Figure 1:
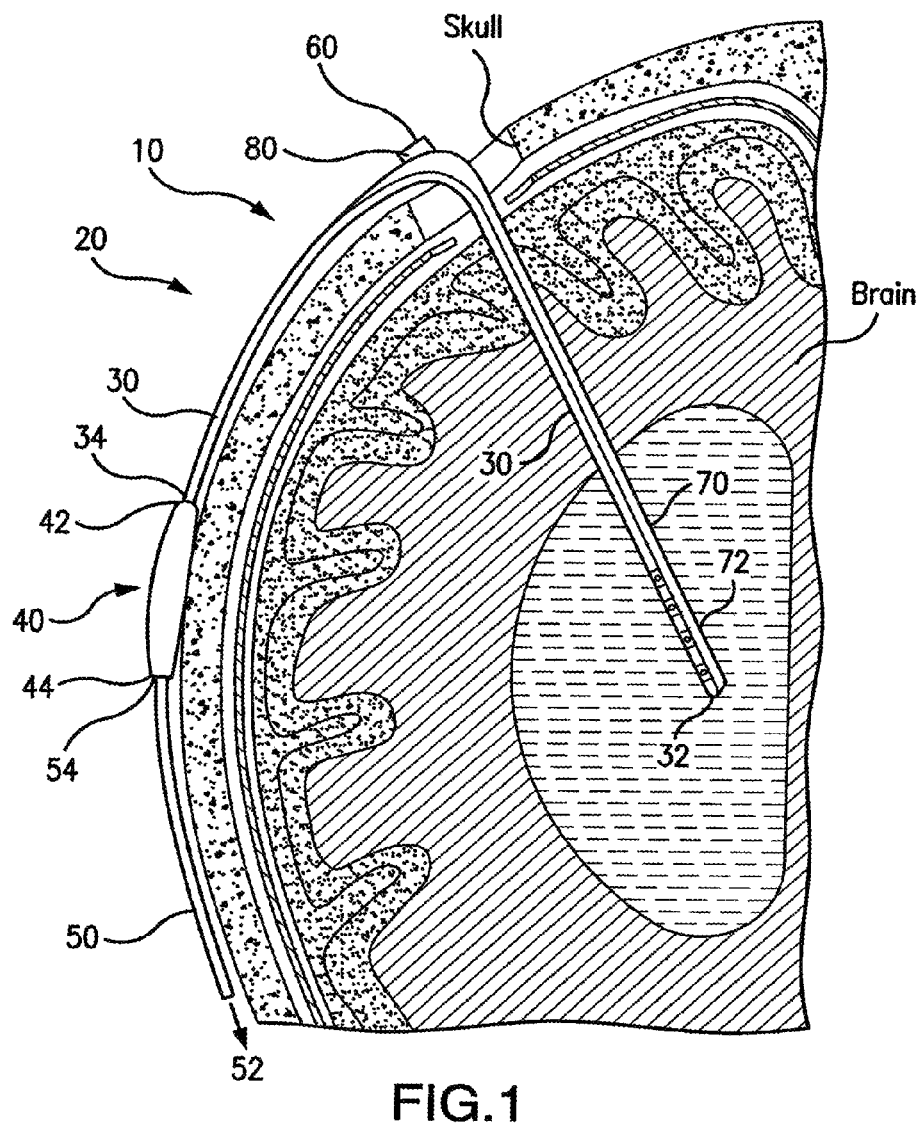
FIG. 1 is a schematic view showing an embodiment of a ventricular shunt system in which a ventricular catheter is positioned in fluid communication with a ventricle of a brain of a subject and a fluid filled reservoir is positioned therein a portion of the ventricle of the patient. In this aspect, the fluid filled reservoir can be mountable adjacent the ventricular catheter. In this aspect, a pressure sensor can be disposed in communication with the fluid within the fluid filled chamber. In this example, a proximal portion of the ventricular shunt system is positioned extra-cranially.
Figure 2:
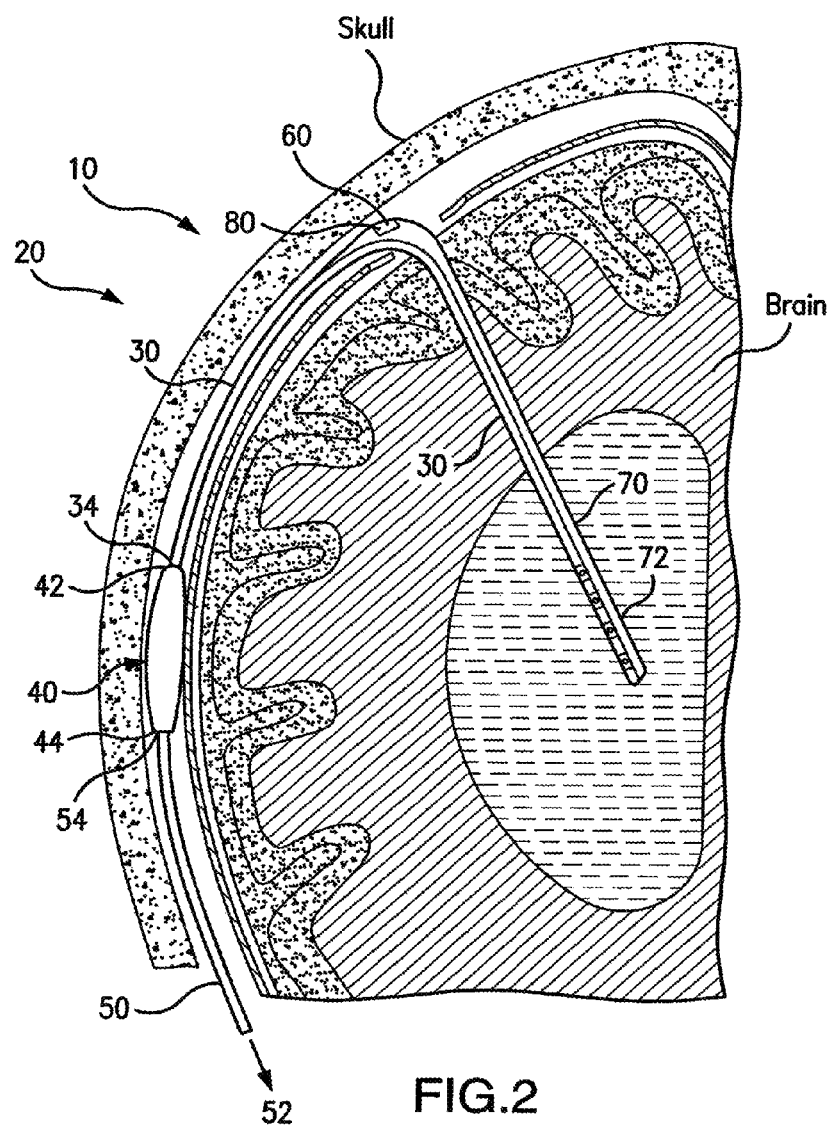
FIG. 2 is a schematic view showing a second embodiment of a ventricular shunt system in which a ventricular catheter is positioned in fluid communication with a ventricle of a brain of a subject and a fluid filled reservoir is positioned therein a portion of the ventricle of the patient. In this aspect, a pressure sensor can be disposed in communication with the fluid within the fluid filled reservoir. In this example, a portion of the ventricular shunt system is exemplarily positioned intra-cranially.
Figure 3:
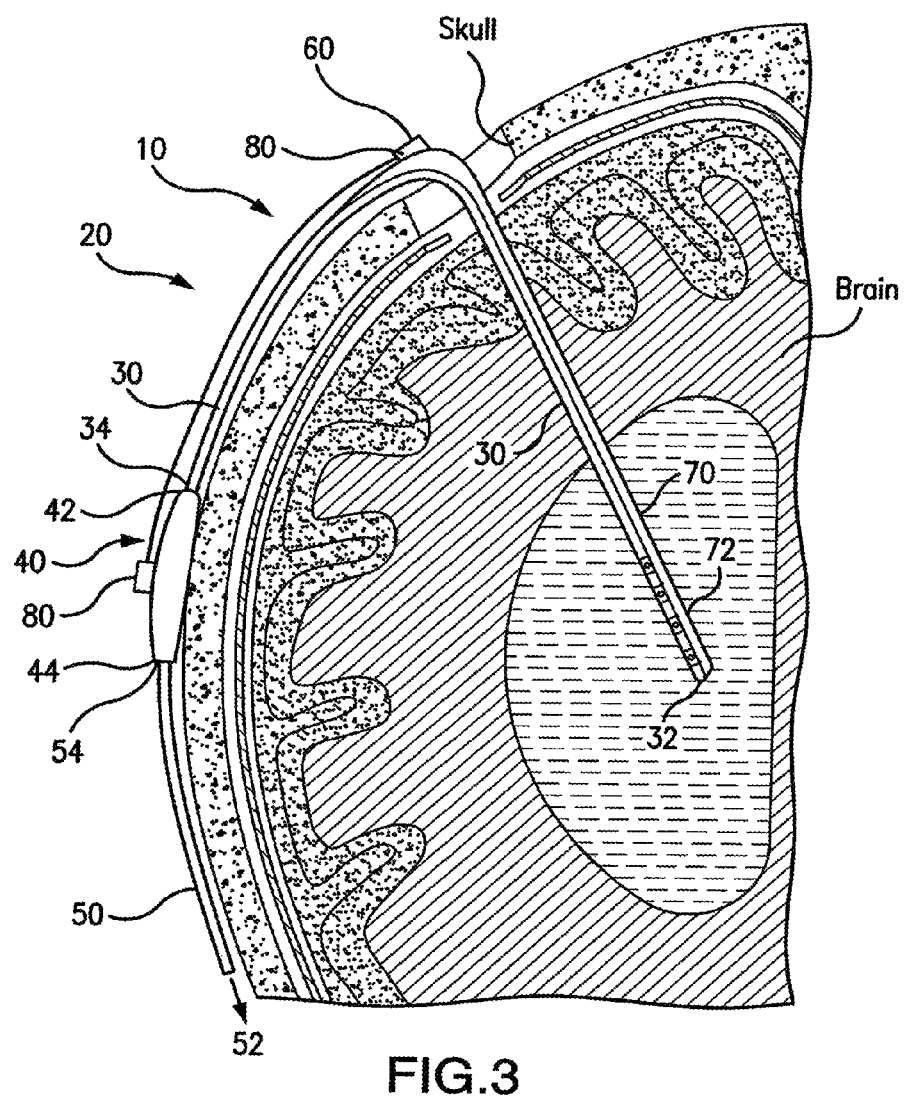
FIG. 3 is a schematic view showing an additional embodiment of a ventricular shunt system in which a ventricular catheter is positioned in fluid communication with a ventricle of a brain of a subject and a fluid filled reservoir is positioned therein a portion of the ventricle of the patient. In this aspect, a pressure sensor is mountable thereon a portion of the surface of the fluid filled reservoir and is electrically coupled to a passive electrical resonant circuit. In this exemplary aspect, a portion of the ventricular shunt system is positioned extra-cranially.
Figure 4:
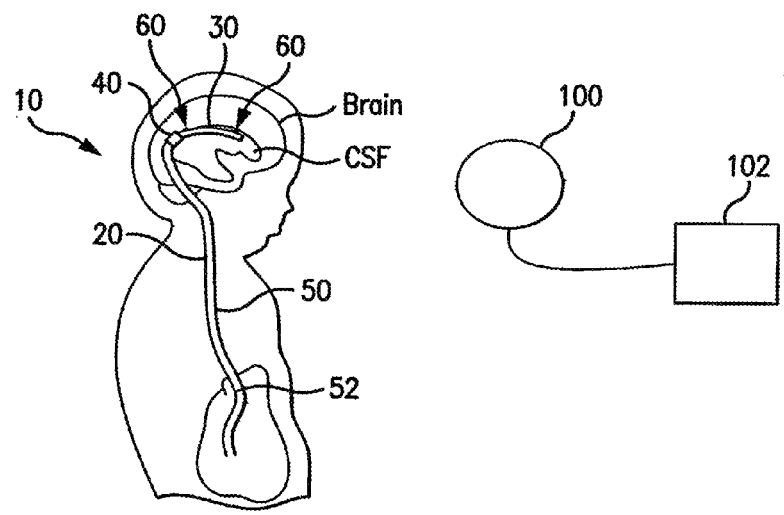
FIG. 4 is a schematic view of a ventricular shunt system in which a ventricular catheter is positioned in fluid communication with a ventricle of a brain of a subject. The ventricular catheter has a first pressure sensor mountable in a proximal portion of the ventricular catheter and a second pressure sensor mountable in a distal portion of the ventricular catheter. In another aspect, a distal end of the ventricular catheter is connected to a valve that is configured to control the flow of fluid therethrough. The valve is coupled to and in fluid communication with a drainage catheter that is in fluid communication with a remote body cavity. Also shown, in one aspect, is an external controller configured to operable communicate with the pressure sensors

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "pressure sensor" can include two or more such pressure sensors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Commonly assigned U.S. patent application Ser. Nos. 12/349,606, 12/175,803, 11/717,967, 11/613,645, 11/472, 905, 11/276,571, 11/157,375, 11/105,294, and 10/943,772 are incorporated herein by reference in their entirety.

Embodiments provided herein comprise a ventricular shunt system can be implanted in fluid communication with a ventricle of a brain of a subject. In one aspect the ventricular shunt system can be used to monitor intracranial pressure and prevent abnormal build-up of cerebrospinal fluid (CSF) in the subject, which can result in hydrocephalus. Referring generally now to FIGS. 1-7, in various aspects, the ventricular shunt system 10 can comprises a catheter assembly 20 comprising a ventricular catheter 30; a valve 40 connected to and in select fluid communication with the ventricular catheter 30, a drainage catheter 50 in fluid communication with the valve, and at least one pressure sensor 60 configured to monitor pressure of fluid within the ventricle of the subject. Optionally, and while the present application discusses in conjunction with a system preventing prevent abnormal build-up of CSF in the subject, it is also contemplated that the system and method described herein can find applicability in treatment of other afflictions in which fluid is desirable moved from one location in the body to another.

In one aspect, the valve 40 has an inlet port 42 and an outlet port 44 and is configured to control a rate of fluid flow between the inlet port and the outlet port. Optionally, it is contemplated that the valve can be an adjustable valve that is selectively configurable to allow selective flow rates therebetween the respective inlet and outlet ports 42, 44 of the valve. For example and without limitation, it is contemplated that the size of the conduit can be adjusted to selected a desired flow rate therethrough the valve. In one example, the conduit size can be manually selectable prior to implantation or when the valve is positioned external to the surface of the body. Optionally, the valve 40 may comprise means for modulating the flow rate of fluid therethrough the valve remotely. In one example, and not meant to be limiting, the valve can be a conventional magnetic valve in which the flow rate therethrough can be selected remotely by the use of remote magnets capable of selectively applying magnetic fields to the valve. In this aspect, the remotely adjustable valve allows for selectable, non-invasive modulation of flowrate through an implanted valve 40.

The ventricular catheter 30 has a distal end 32 and a proximal end 34. In one aspect, the proximal end of the ventricular catheter 30 is coupled to the inlet port 42 of the valve 40. Similarly, the drainage catheter 50 has a distal end 52 and a proximal end 54. In this aspect, the proximal end of the drainage catheter 40 is coupled to the outlet port 44 of the valve 40. In one aspect, it is contemplated that at least a portion of the ventricular catheter 40 can be positioned in fluid communication with a ventricle of a brain of a subject and at least a portion of the drainage catheter 50 is positioned in fluid communication with a remote body cavity for adsorption therein. In another aspect, at least a portion of the distal end 42 of the ventricular catheter 40 can be positioned in fluid communication with a ventricle of a brain of a subject and at least a portion of the distal end 52 of the drainage catheter 50 is positioned in fluid communication with a remote body cavity.

In one aspect, the at least one pressure sensor 60 can be mountable thereon a portion of the ventricular shunt system. In various aspects, it is contemplated that the at least one pressure sensor 60 can be configured to monitor the pressure of fluid within one or more portions of the ventricular shunt system 10. For example, in one aspect, the at least one pressure sensor can be selectably mountable thereon a portion of the catheter assembly 20 to effect the desired measurement of the fluid pressure within the ventricular shunt system 10. It is contemplated that the at least one pressure sensor 60 can be wireless or the at least one pressure sensor can be electrically coupled by, for example and without limitation, via wires to a controller that can be selectively positionable intra-cranially or extra-cranially as desired.

For example, and without limitation, one pressure sensor 60 of the at least one pressure sensor can be mounted therein the ventricular catheter adjacent the distal end 32 of the ventricular catheter. In various aspects, it is contemplated that the at least one pressure sensor 60 can be mounted on selected portions of the respective ventricular catheter 30, the valve 40, and the drainage catheter 50. In one aspect, the at least one pressure sensor 60 can comprise a plurality of pressure sensors. In another aspect, it is also contemplated that each pressure sensor 60 of the plurality of pressure sensors can be individually addressable. Thus, it is contemplated that the plurality of pressure sensors can comprise a plurality of individually addressable pressure sensors.

In yet another aspect, it is contemplated that each pressure sensor 60 of the plurality of pressure sensors can be mounted thereon or therein catheter assembly in spaced relationship. For example and without limitation, the plurality of pressure sensors 60 can be mounted in spaced relationship on the ventricular catheter 30, the valve 40, and/or the drainage catheter 50 (or on any desired combination thereof).

In one non-limiting example, it is contemplated that at least individually addressable one pressure sensor can be mounted on a desired portion of the ventricular catheter 30, such as, for example, proximal or at the distal end 32, and at least one individually addressable pressure sensor 60 can be mounted on a desired portion of the drainage catheter 50, such as, for example, the distal end 52. In another aspect, the plurality of individually addressable pressure sensors 60 can be mounted in the ventricular catheter 30 is spaced relationship. As one will appreciate, the spacing of the respective individually addressable pressure sensors along the ventricular catheter allows for the monitoring of the patency of the ventricular catheter. Similarly, it is contemplated that the plurality of individually addressable pressure sensors can be mounted in the drainage catheter is spaced relationship so that the patency of the drainage catheter can be selectively monitored.

In one aspect, the at least one pressure sensor 60 can be a conventional pressure sensor. In another aspect, the at least one pressure sensor 60 can comprise a passive electrical resonant circuit 80 that is configured to be selectively electromagnetically coupled to an ex-vivo source of RF energy, which can be produced, for example and as described in more detail below, be a remote or ex-vivo interrogator. In this aspect, each pressure sensor 60, in response to the electromagnetic coupling, can be configured to generate an output signal 82 characterized by a frequency that is dependent upon urged movement of a portion of the passive electrical resonant circuit 80 and is indicative of pressure applied thereon a portion of the respective at least one pressure sensor.

In one aspect, the at least one pressure sensor 60 can be positioned in fluid communication with the fluid therein the ventricle of the patient. In this aspect, upon application of a moment or force thereon the at least one pressure sensor, at least a portion of the passive electrical resonant circuit 80 of the at least one pressure sensor can be forced or otherwise urged to move with a resultant change in the resonant frequency of the at least one pressure sensor when it is energized via the electromagnetic coupling. The sensed frequency of the at least one pressure sensor is indicative of the fluid pressure therein the ventricle of the patient.

In another aspect, the at least one pressure sensor 60 can be positioned in communication with a sealed reservoir 70 that is configured to contain a non-compressible fluid. Optionally, it is contemplated that the at least one pressure sensor can be positioned within the reservoir or positioned within a wall of the reservoir. In this aspect, at least a portion of the sealed reservoir can be configured to be selectively positioned therein a portion of the ventricle of the patient. In another aspect, it is contemplated that the at least one pressure sensor 60 can be mounted to one or more portions of the sealed reservoir 70.

In this aspect, the sealed reservoir 70 can be filled with a known and invariant amount of fluid. In other aspects, it is contemplated that the sealed reservoir can be partially filled with fluid or the sealed reservoir can be completely filled with fluid. In one non-limiting example, the fluid in the sealed reservoir 70 can comprise saline. It is contemplated however that other suitable non-compressible fluids can be selected by one skilled in the art.

In one exemplary aspect, the sealed reservoir 70 can be mountable adjacent the ventricular catheter 30 such that at least a distal end 72 of the reservoir can be positioned proximate the distal end 32 of the ventricular catheter and in communication with the fluid therein the ventricle. In one aspect, at least a portion of the distal end 72 of the reservoir that is exposed to the fluid therein the reservoir can comprise a pliable or pliant material. In this aspect, application of a force thereon the pliable surface of the sealed reservoir 70 causes a like force to be exerted thereon the at least one pressure sensor, which results in at least a portion of the passive electrical resonant circuit 80 of the at least one pressure sensor 60 to be forced or otherwise urged to move with a resultant change in the resonant frequency of the at least one pressure sensor when it is energized via the electromagnetic coupling. As noted above, the sensed frequency of the at least one pressure sensor 60 is indicative of the fluid pressure therein the ventricle of the patient.

As noted above, it is contemplated, in one exemplary non-limiting aspect, that the at least one pressure sensor can comprise a passive electrical resonant circuit that can be configured to be selectively interrogated with RF energy produced by a remote interrogator. The transmitted RF energy can be selected in order to selectively electromagnetically couple the passive electrical resonant circuit. In another aspect, the passive electrical resonant circuit of the at least one pressure sensor 60 can comprise a non-linear element that is configured to respond in a non-linear manner to an energizing signal.

As one will appreciate and as described in more detail below, the remote interrogator 100 can act as an ex-vivo source of desired RF energy. In another aspect, the passive electrical resonant circuit 80, upon energizing via electromagnetic coupling, can be configured to generate an output signal 82 characterized by a frequency that is dependent upon an urged movement of a portion of the passive electrical resonant circuit. The frequency within the output signal is indicative of pressure that is applied thereon a portion of the respective at least one pressure sensor. One will appreciate that the output frequency can be the resonant frequency of the at least one pressure sensor. One skilled in the art will appreciate that the change in the resonant frequency allows for the ventricular shunt system 10 to determine the relative applied pressure of the fluid within the ventricle of the patient or within select portions of the ventricular shunt system.

In one aspect, the passive electrical resonant circuit 80 of the at least one pressure sensor 60 can be an electromechanical transducer that is capable of transforming a signal from one form of energy into another, namely from mechanical into electrical energy. In one aspect, it is contemplated that the passive electrical resonant circuit 80 of the at least one pressure sensor can comprise an inductance-capacitance ("LC") resonant circuit. Optionally, in another aspect, the passive electrical resonant circuit 80 of the at least one pressure sensor can comprise a self-resonant inductor circuit.

Conventionally, a passive (no battery) LC resonant circuit is composed of two electrical passive components that are connected in series: (a) a coil, or inductor ("L"), (b) a capacitor ("C"). Such a passive electrical circuit exhibits electrical resonance when subjected to an alternating electromagnetic field. The electrical resonance is particularly acute for a specific frequency value or range of the impinging signal. When the impinging signal substantially reaches the resonant frequency of the LC resonant circuit inside the at least one pressure sensor, a pronounced disturbance of the field can be detected wirelessly. In the simplest approximation, the electrical resonance occurs for a frequency f, related to the value of L and C according to Equation 1:

$$f = (2\pi(LC)^{1/2})^{-1} \quad \text{(Equation 1)}$$

The passive electrical resonant circuit for the at least one pressure sensor described herein that utilize a passive electrical resonant circuit can be fabricated, for example and without limitation, via Micro Electro-Mechancial Systems ("MEMS") approach to sensor design, which lends itself to the fabrication of small sensors that can be formed using biocompatible polymers as substrate materials. In a further aspect, appropriately biocompatible coatings can be applied to the surfaces of the respective pressure sensors in order to prevent adhesion of biological substances to the respective pressure sensors that could interfere with their proper function.

In one example, the passive electrical resonant circuit of the at least one pressure sensor 60 can be manufactured using Micro-machining techniques that were developed for the integrated circuit industry. An example of this type of sensor features an LC resonant circuit with a variable capacitor is described in Allen et al., U.S. Pat. No. 6,111,520, which is incorporated herein in its entirety by reference. In this sensor, the capacitance varies with the pressure of the environment in which the capacitor is placed. Consequently, the resonant frequency of the exemplary LC circuit of the Allen pressure sensor varies depending on the pressure of the surrounding ambient environment.

As described above, it is contemplated that the LC resonant circuit can comprise a coil inductor operably coupled to a capacitor. In various aspects, the inductance of the LC resonant circuit can be between about 0.1 to about 1000 micro-Henry, preferably between about 1 to about 100 micro-Henry, and more preferably between about 5 to about 15 micro-Henry. The capacitance of the LC resonant circuit can be between about 0.1 to about 1000 pF, preferably between about 0.5 to about 100 pF, and more preferably between about 1 to about 20 pF. The resonant frequency of the LC resonant circuit can be between about 0.1 to about 450 MHz, preferably between about 1 to about 60 MHz, and more preferably between about 25 to about 45 MHz. In addition, the quality factor at self resonance and the frequency range of the self-resonant frequency itself can be between about 5 to 120, preferably between about 5 to about 80, and more preferably between about 10 to about 70.

There are various manufacturing techniques that can be employed to realize the at least one pressure sensor. Capacitors and inductors made by a variety of methods can be manufactured separately, joined through interconnect methods and encapsulated in hermetic packaging. In one embodiment, the pressure sensitive capacitor and the three-dimensional inductor coil are formed separately and joined together to form the LC circuit. In another embodiment, the capacitor and inductor coil can be manufactured integral with one another. Additionally, there are several methods to create these discrete elements and to join each discrete element to create the at least one pressure sensor.

Q factor (Q) is the ratio of energy stored versus energy dissipated. The reason Q is important is that the ring down rate of the at least one pressure sensor is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, in one aspect, the at least one pressure sensor can be configured with values of Q sufficiently high enough to avoid unnecessary increases in complexity in communicating with the at least one pressure sensor via external electronics.

The Q of the at least one pressure sensor 60 can be dependent on multiple factors such as, for example and without limitation, the shape, size, diameter, number of turns, spacing between the turns and cross-sectional area of the inductor component. In addition Q will be affected by the materials used to construct the at least one pressure sensor. In one example, the at least one pressure sensor can be formed from materials with low loss tangents to effect a pressure sensor with higher Q factors.

In one exemplary aspect, the coil inductor of the LC resonant circuit can be a substantially planar spiral inductor. Optionally, the coil inductor of the LC resonant circuit can have a longitudinal axis and the respective windings of the coil inductor can spiral about and extend along the longitudinal axis.

In one aspect, the inductor coil can be comprised of the inductor coil body and the coil leads. One skilled in the art will appreciate that numerous parameters of the inductor coil can be varied to optimize the balance of size and the electrical properties of the circuit, including the materials, coil diameter, wire gage, number of coil windings, and cross-sectional area of the coil body. Typically, the material of the coil must be highly conductive and also biocompatible. Suitable materials include, but are not limited to, gold, copper and alloys thereof. If the wire is sufficiently strong, the coil can be self-supporting, also known as an "air core" configuration. A solenoid coil is another suitable configuration. If the wire is not sufficiently strong to be unsupported to maintain its intended configuration during assembly and in use, the coil can be formed around a central bobbin comprised of a suitable dielectric material. In the alternative, the wound coil can be encased in a liquid polymer that can cure or otherwise harden after it is applied to the coil body. Polyimide is one preferred material for this application because of its thermal, electrical, and mechanical properties. However, processes achieving substantially similar results that involve lower processing temperatures would make other polymer choices desirable, such choices being obvious to one skilled in the art.

Optionally, it is contemplated that the passive electrical circuit of the at least one pressure sensor 60 can be housed within a substantially non-permeable enclosure to ensure the protection of the passive electrical circuit of the at least one pressure sensor 60 when the respective at least one pressure sensor 60 is positioned within the living being. In this aspect, the passive electrical circuit of the at least one pressure sensor 60 can be protected from deleterious agents such as corrosion, parasitic excessive strain/stress, biological response, etc. . . . . . As one will appreciate, it is contemplated that the enclosure can be formed of materials that substantially prevent any undesired fluids and/or gases from passing or diffusing through the walls of the enclosure, utilizing manufacturing processes that eliminate undesired holes that could otherwise permit such passing of undesired fluids or gases.

In another aspect, the enclosure can be formed of materials that do not allow any undesired fluids and/or gases from passing or diffusing through the walls of the enclosure. Exemplary enclosure material can include, without limitation, biocompatible polymer (such as, for example and without limitation, PEAK, PE, PTFE, FEP, semi-crystalline thermoplastic polymers, and the like), glass, fused-silica, low temperature glass, ceramics, quartz, pyrex, sapphire, sintered zirconia and the like. An acceptable level of permeability can be a rate of fluid ingress or egress that changes the original capacitance of the LC circuit by an amount preferably less than 10 percent, more preferably less than 5 percent, and most preferably less than 1 percent over the accumulated time over which measurements will be taken.

Optionally, it is also contemplated that the housing can define an internal cavity in which at least a portion of the passive electrical circuitry 80 can be disposed. In a further aspect, a known and invariant quantity of gas can be added to the internal cavity of the housing. In another aspect, it is contemplated that the enclosure can be formed of materials that will not allow the resonant circuit of the pressure sensor to flex in response to relative motion of the implant that the at least one pressure sensor 60 is mounted thereon or other forces that can be otherwise applied to the exterior surface of the pressure sensor.

In another aspect, the exemplary enclosure materials help to provide the desired biocompatibility, non-permeability and/or manufacturing processing capabilities of the pressure sensor containing the resonant circuit. These exemplary materials are considered dielectrics, that is, they are poor conductors of electricity but are efficient supporters of electrostatic or electroquasistatic fields. A dielectric material has the ability to support such fields while dissipating minimal energy. In this aspect, the lower the dielectric loss, the lower the proportion of energy lost, and the more effective the dielectric material is in maintaining high Q.

With regard to operation within the human body, there is a second important issue related to Q, namely that blood and body fluids are conductive mediums and are thus particularly lossy. As a consequence, when an pressure sensor having a resonant circuit is immersed in a conductive fluid, energy from the at least one pressure sensor 60 will dissipate, substantially lowering the Q and reducing the pressure sensor-to-electronics distance. In one aspect, the loss can be minimized by further separation of the pressure sensor having the resonant circuit from the conductive liquid, which can be accomplished, for example and without limitation, by coating at least a portion of the pressure sensor having the resonant circuit in a suitable low-loss-tangent dielectric material.

As described above, in one embodiment, a pressure sensor 60 having a resonant circuit 80 can comprise a passive LC resonant circuit with a varying capacitor. Because the exemplary pressure sensor can be fabricated using passive electrical components and has no active circuitry, it does not require on-board power sources such as batteries, nor does it require leads to connect to external circuitry or power sources. These features create a pressure sensor 60 that is self-contained within the enclosure and lacks physical interconnections that traverse the hermetic enclosure or housing.

Because of the presence of the inductor in the LC resonant circuits described herein, it is possible to couple to the pressure sensor 60 having the LC resonant circuit electromagnetically and to induce a current in the LC resonant circuit 80 via a magnetic loop. This characteristic allows for wireless exchange of electromagnetic energy with the pressure sensor and the ability to operate it without the need for an on-board energy source such as a battery. Thus, using the system described herein, it is possible to determine the respective pressure of fluid acting on the respective pressure sensors in a simple, non-invasive procedure by remotely interrogating the pressure sensor or pressure sensors, detecting and recording the resonant frequency, and converting this value to a pressure measurement.

In a further aspect, the system for sensing pressure or pressures within a catheter assembly implanted in a living being described herein can comprise an ex-vivo source of RF energy and the at least one passive electrical resonant circuit pressure sensor described above.

In a further aspect, the system can comprises a means for monitoring the output signal 82 of the pressure sensor, which frequency can comprises the resonant frequency of the pressure sensor. In one exemplary aspect, the means for monitoring the output signal of the pressure sensor can comprise a means for detecting or otherwise receiving the output signal of the pressure sensor and a processor, or similar processing means, configured to determine the pressure of fluid acting on the respective pressure sensor 60 based on the frequency of the output signal produced by the pressure sensor. It is of course contemplated that, if the at least one pressure sensor comprises a plurality of individually addressable pressure sensors, the system can optionally comprise a means for monitoring the resonant frequency of the output signals from any of the selected pressure sensors to determine the pressure of fluid acting on the respective pressure sensor 60 based on the frequency of the output signal 62 of the addressed pressure sensor.

In another aspect, the system described herein provides for a system capable of determining the resonant frequency and bandwidth of the at least one pressure sensor using an impedance approach. In this approach, an excitation signal can be transmitted using a transmitting antenna to electromagnetically couple a pressure sensor having a passive electrical resonant circuit to the transmitting antenna, which resultantly modifies the impedance of the transmitting antenna. The measured change in impedance of the transmitting antenna allows for the determination of the resonant frequency and bandwidth of the passive electrical resonant circuit of the pressure sensor.

In a further aspect, the system described herein provides for a transmit and receive interrogation system configured to determine the resonant frequency and bandwidth of a resonant circuit within a particular pressure sensor. In this exemplary process, an excitation signal of white noise or predetermined multiple frequencies can be transmitted from a transmitting antenna and the passive electrical resonant circuit 80 of the pressure sensor 60 is electromagnetically coupled to the transmitting antenna. A current is induced in the passive electrical resonant circuit of the pressure sensor as it absorbs energy from the transmitted excitation signal, which results in the oscillation of the passive electrical circuit at its resonant frequency. A receiving antenna, which can also be electromagnetically coupled to the transmitting antenna, receives the excitation signal minus the energy which was absorbed by the pressure sensor. Thus, the power of the received or output signal experiences a dip or notch at the resonant frequency of the pressure sensor. The resonant frequency and bandwidth can be determined from this notch in the power.

In one aspect, the transmit and receive methodology of determining the resonant frequency and bandwidth of a passive electrical resonant circuit of an pressure sensor can include transmitting a multiple frequency signal from a transmitting antenna to electromagnetically couple the passive electrical resonant circuit on the at least one pressure sensor 60 to the transmitting antenna in order to induce a current in the passive electrical resonant circuit of the pressure sensor. A modified transmitted signal due to the induction of current in the passive electrical circuit is received and processed to determine the resonant frequency and bandwidth.

In another aspect, the system can determine the resonant frequency and bandwidth of a passive electrical resonant circuit within a particular pressure sensor by using a chirp interrogation system, which provides for a transmitting antenna that is electromagnetically coupled to the resonant circuit of the pressure sensor. In this aspect, an excitation signal of white noise or predetermined multiple frequencies can be applied to the transmitting antenna for a predetermined period of time to induce a current in the passive electrical resonant circuit of the pressure sensor at the resonant frequency. The system then listens or otherwise receives an output signal that radiates from the energized passive electrical resonant circuit of the pressure sensor. In this aspect, the resonant frequency and bandwidth of the passive electrical resonant circuit can be determined from the output signal.

In this aspect, the chirp interrogation method can include transmitting a multi-frequency signal pulse from a transmitting antenna; electromagnetically coupling a passive electrical resonant circuit on a pressure sensor to the transmitting antenna to induce a current in the resonant circuit; listening for and receiving an output signal radiated from the energized passive electrical signal of the pressure sensor; determining the resonant frequency and bandwidth from the output signal, and resultantly, determining the pressure of fluid acting on the respective pressure sensor 60 from the determined resonant frequency and bandwidth.

In a further aspect, the system described herein can provide an analog system and method for determining the resonant frequency of a passive electrical resonant circuit within a particular pressure sensor. The analog system can comprise a transmitting antenna coupled as part of a tank circuit, which, in turn, is coupled to an oscillator. In this aspect, a signal is generated which oscillates at a frequency determined by the electrical characteristics of the tank circuit. The frequency of this signal is further modified by the electromagnetic coupling of the passive electrical resonant circuit of the pressure sensor. This signal can be applied to a frequency discriminator that provides a signal from which the resonant frequency of the resonant circuit can be determined. In this aspect, the analog method can include generating a transmission signal using a tank circuit that includes a transmitting antenna; modifying the frequency of the transmission signal by electromagnetically coupling the passive electrical resonant circuit of the pressure sensor to the transmitting antenna; and converting the modified transmission signal into a standard signal for further application.

One exemplary method of interrogation is explained in more detail in commonly assigned U.S. patent application Ser. No. 11/105,294. In the described methodology, the interrogating system energizes the pressure sensor having the resonant circuit with a low duty cycle, gated burst of RF energy having a predetermined frequency or set of frequencies and a predetermined amplitude. The energizing signal is coupled to the passive electrical resonant circuit via a magnetic loop. The energizing signal induces a current in the passive electrical resonant circuit that is maximized when the frequency of the energizing signal is substantially the same as the resonant frequency of the passive electrical resonant circuit. The system receives the ring down response of the pressure sensor via magnetic coupling and determines the resonant frequency of the pressure sensor, which is then used to determine the pressure of fluid acting on the respective pressure sensor 60. In one aspect, the resonant frequency of the pressure sensor is determined by adjusting the frequency of the energizing signal until the phase of the ring down signal and the phase of a reference signal are equal or at a constant offset. In this manner, the energizing signal frequency is locked to the pressure sensor's resonant frequency and the resonant frequency of the pressure sensor is known. The relative pressure can then be ascertained.

In one aspect, the system can comprise a coupling loop that can be selectively positioned relative to the at least one pressure sensor 60 to maximize the electromagnetic coupling between the passive electrical resonant circuit of the pressure sensor and the coupling loop. The system can also provide the necessary isolation between the energizing signal and the output signal. In one aspect, it is contemplated that the system can energize the passive electrical resonant circuit of the pressure sensor with a low duty cycle, gated burst of RF energy having a predetermined frequency or set of frequencies and a predetermined amplitude. The energizing signal can be electromagnetically coupled to the passive electrical resonant circuit of the pressure sensor via one or more energizing loops. In operation, each energizing loop can be tuned to a different resonant frequency. The selection of the desired resonant frequencies can be based on the desired bandwidth, which, in one aspect of the invention and without limitation can range between about 30 to about 37.5 MHz.

The energizing signal induces a current in the passive electrical resonant circuit of the pressure sensor that is maximized when the energizing frequency is the same as the resonant frequency of the passive electrical resonant circuit of the pressure sensor. The system receives the ring down response of the pressure sensor (or sensors) via one or more coupling loops and determines the resonant frequency of the sensor, which can be used to calculate the pressure of fluid acting on the respective pressure sensor 60.

In one aspect, a pair of phase locked loops ("PLLs") can be used to adjust the phase and the frequency of the energizing signal until its frequency locks to the resonant frequency of the passive electrical resonant circuit of the pressure sensor. In one embodiment, one PLL samples during the calibration cycle and the other PLL samples during the measurement cycle. In one non-limiting example, these cycles can alternate every 10 microseconds and can be synchronized with the pulse repetition period. In one aspect, the calibration cycle adjusts the phase of the energizing signal to a fixed reference phase to compensate for any system delay or varying environmental conditions. The environmental conditions that can affect the accuracy of the reading can include, but are not limited to, proximity of reflecting or magnetically absorbative objects, variation of reflecting objects located within transmission distance, variation of temperature or humidity which can change parameters of internal components, and aging of internal components.

In one aspect, one of the PLLs can be used to adjust the phase of the energizing signal and is referred to herein as the fast PLL. The other PLL can be used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator. The cycle in which the calibration signal is sampled is referred to as the calibration cycle. In one aspect, the system can adjust the phase of the energizing signal to drive the phase difference to zero or another select reference phase.

During the measurement cycle, the signal coupled from the passive electrical resonant circuit of the pressure sensor (referred to herein as the output signal) can be processed and sampled to determine the phase difference between the output signal and the energizing signal. The system can then adjust the frequency of the energizing signal to drive the phase difference to zero or other reference phase. Once the slow PLL is locked, the frequency of the energizing signal is deemed to match the resonant frequency of the passive electrical resonant circuit of the pressure sensor. The operation of the slow PLL is qualified based on signal strength so that the slow PLL does not lock unless the strength of the output signal meets a predetermined signal strength threshold.

In one aspect, a single un-tuned coupling loop can be is used. In this exemplary aspect, the loop can be connected to an input impedance that is high relative to the loop inductance. Optionally, multiple coupling loops can be used and each loop is tuned to a different resonant frequency.

In another aspect, the loops can be connected to a base unit 102 that generates the energizing signal and processes the output signal via a cable assembly. In this aspect, the cable assembly provides isolation between the energizing signal and the sensor signal by maximizing the distance between the coaxial cables that carry the signals and maintaining the relative positions of the coaxial cables throughout the cable assembly. In another exemplary aspect, the coaxial cables can be positioned on opposite sides of an internal cable, approximately 180 degrees apart. Shielding can also be used to isolate the energizing signal from the output signal. In one aspect, it is contemplated that additional shielding can be provided around each of the respective coaxial cables.

Figure 11:
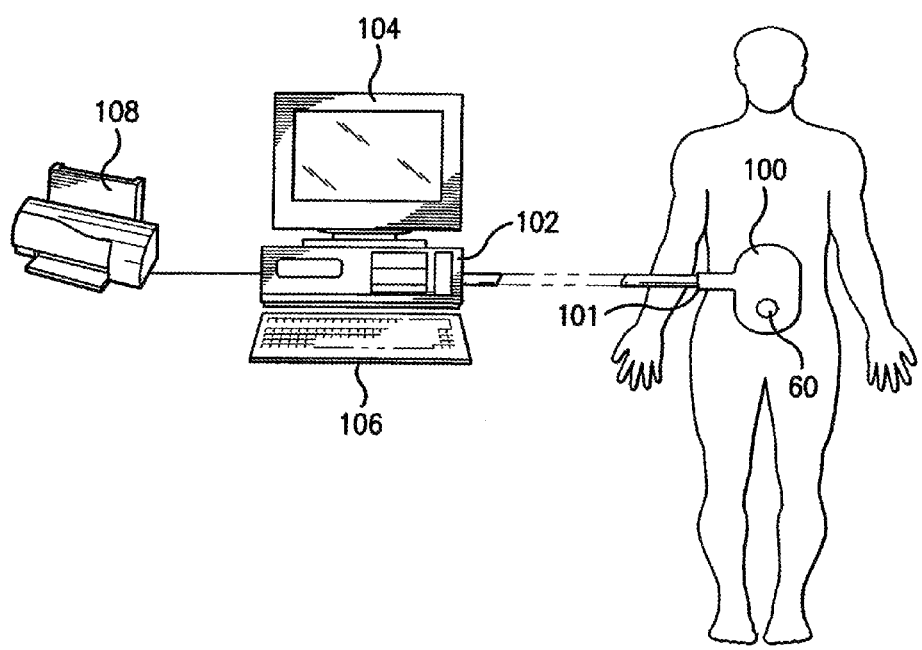
FIG. 11 illustrates an exemplary interrogation system for communicating with the at least one wireless pressure sensor that is positioned within a body.

In one aspect, FIG. 11 illustrates an exemplary interrogation system for communicating with the wireless apparatus described above that is positioned within a body. Without limitation, it is contemplated that the system can be used in at least two environments: the operating room during implant and the physician's office during follow-up examinations.

In one exemplary embodiment, the interrogation system can comprise a coupling loop 100, the base unit 102, a display device 104, and an input device 106, such as, for example and without limitation, a keyboard. In one exemplary embodiment, the base unit can include an RF amplifier, a receiver, and signal processing circuitry. In one aspect, the coupling loop 100 can be configured to charge the passive electrical resonant circuit 80 of the pressure sensor 60 and then couple signals from the energized passive electrical resonant circuit of the pressure sensor into the receiver. Schematic details of the exemplary circuitry are illustrated in FIG. 11.

The display 104 and the input device 106 can be used in connection with the user interface for the system. In the embodiment illustrated in FIG. 11, the display device and the input device are conventionally connected to the base unit. In this embodiment, the base unit can also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface.

In one aspect, LABVIEW software can be used to provide the user interface, as well as to provide graphics, store and organize data and perform calculations for calibration and normalization. The user interface can record and display patient data and guide a user through surgical and follow-up procedures. In another aspect, an optional printer 108 can be operably connected to the base unit and can be used to print out patient data or other types of information. As will be apparent to those skilled in the art in light of this disclosure, other configurations of the system, as well as additional or fewer components can be utilized with embodiments of the invention.

In one embodiment, the coupling loop can be formed from a band of copper. In this aspect, it is contemplated that the coupling loop comprises switching and filtering circuitry that is enclosed within a shielded box. The loop can be configured to charge the passive electrical resonant circuit 80 of the at least one pressure sensor 60 and then couple signals from the energized passive electrical resonant circuit of the pressure sensor into a receiver. It is contemplated that the antenna can be shielded to attenuate in-band noise and electromagnetic emissions.

Figure 12:
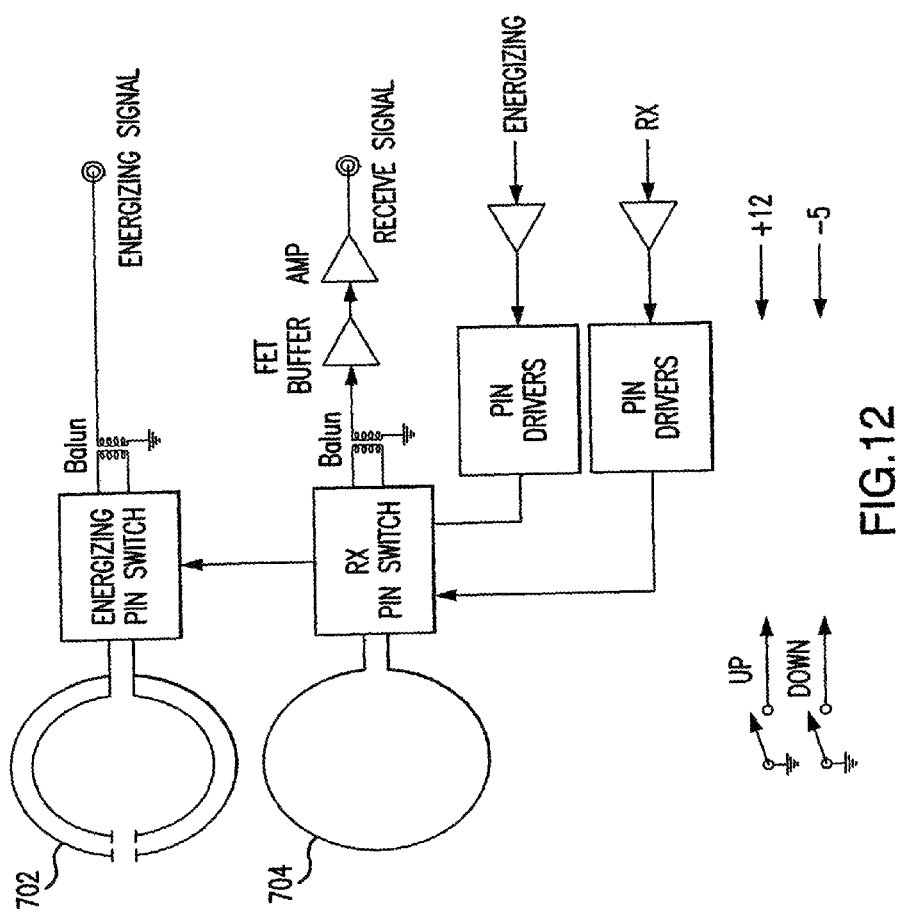
FIG. 12 is an exemplary block diagram of an exemplary coupling loop assembly for communication with at least one wireless pressure sensor.

In an alternative embodiment for a coupling loop, as shown in FIG. 12, separate loops for energizing 702 and for receiving 704 are provided, although a single loop can be used for both functions. PIN diode switching inside the loop pressure sensor can be used to provide isolation between the energizing phase and the receive phase by opening the RX path pin diodes during the energizing period, and opening the energizing path pin diodes during the coupling period. It is contemplated in this embodiment that multiple energizing loops can be staggered tuned to achieve a wider bandwidth of matching between the transmit coils and the transmit circuitry.

In one aspect, the coupling loop or antenna can provide isolation between the energizing signal and the output signal, support sampling/reception of the output signal soon after the end of the energizing signal, and minimize switching transients that can result from switching between the energizing and the coupled mode. The coupling loop can also provide a relatively wide bandwidth, for example from between about X to about Y and preferably from between about 30 to about 37.5 MHz.

In one embodiment, separate loops can be used for transmitting the energizing signal to the passive electrical resonant circuit of the pressure sensor and coupling the output signal from the energized passive electrical resonant circuit of the pressure sensor. Two stagger-tuned loops can be used to transmit the energizing signal and an un-tuned loop with a high input impedance at the receiver can be used to receive the output signal. The term "coupling loop" is used herein to refer to both the loop(s) used to receive the output signal from the energized passive electrical resonant circuit of the pressure sensor (the "pressure sensor coupling loop"), as well as the loop pressure sensor that includes the loop(s) used to transmit the energizing signal to the passive electrical resonant circuit of the pressure sensor (the "energizing loop") and the pressure sensor coupling loop(s).

During the measurement cycle, the pressure sensor coupling loop can be configured to couple the output signal from the energized passive electrical resonant circuit of the pressure sensor, which is relatively weak and dissipates quickly. In one aspect, the voltage provided to the receiver in the base unit depends upon the design of the pressure sensor coupling loop and in particular, the resonant frequency of the loop.

Figure 13B:
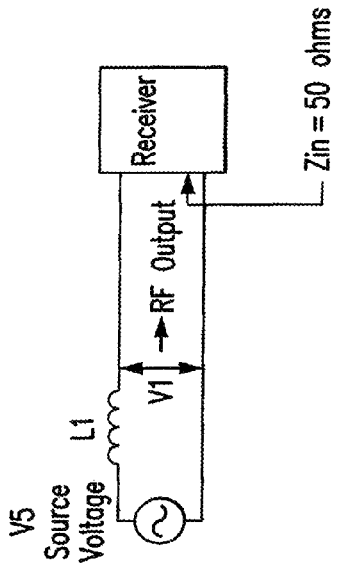
FIG. 13A illustrates a exemplary coupling loop that is un-tuned and FIG. 13B illustrates its equivalent circuit.
Figure 13A:
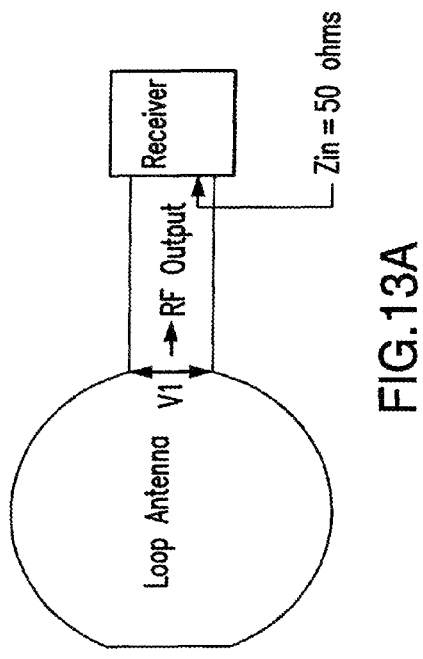

In a further aspect, it is contemplated that the coupling loop can be un-tuned or tuned. FIG. 13A illustrates a loop that is un-tuned and FIG. 13B illustrates its equivalent circuit. The loop has an inductance, $L_1$, and is terminated into the receiver using a common input impedance, which can, for example and without limitation, be 50 ohms. The voltage at the receiver, $V_1$, is less than the open circuit voltage of the loop, i.e., the voltage that would be coupled by the loop if the loop was not terminated, $V_s$, and can be calculated as shown below.

$$V_1 = V_s \frac{50}{50 + j\omega L_1} \qquad \text{Equation 2}$$

Where L1 is the inductance of the loop and $\omega=2\pi f$, with f=frequency in hertz.

Figure 14B:
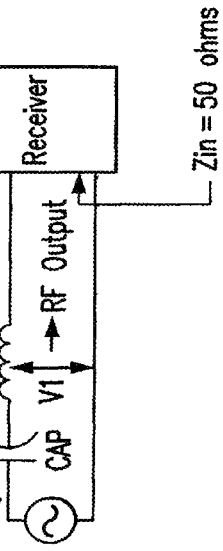
FIG. 14A illustrates a loop that is tuned and FIG. 14B illustrates its equivalent circuit.
Figure 14A:
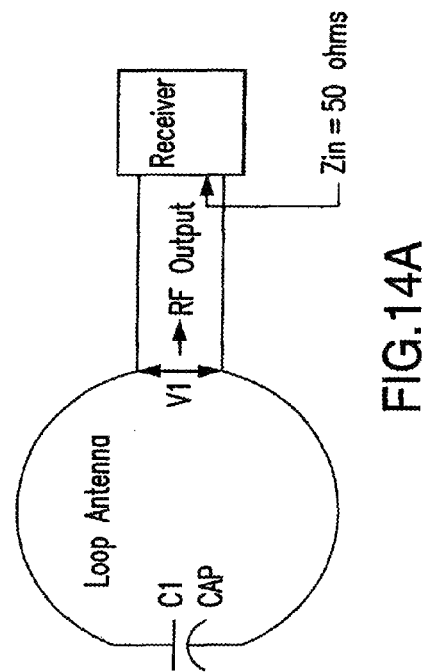

To maximize the voltage at the receiver, it is contemplated that the loop can be tuned. FIG. 14A illustrates a loop that is tuned and FIG. 14B illustrates its equivalent circuit. In this aspect, the loop has an inductance, $L_1$, and a capacitance, $C_1$. The capacitance, $C_1$, is selected so that it cancels the inductance, $L_1$ at the resonant frequency, i.e., the series resonant circuit, $C_1$-$L_1$, is 0 ohms at the resonant frequency. At the resonant frequency the voltage at the receiver, $V_1$, equals the voltage coupled by the loop, $V_s$. One disadvantage of this type of loop is that it is optimized for a single frequency. If the loop is used in an environment where the frequency of the output signal is changing, then the capacitance is either changed dynamically or set to a compromise value (e.g., the loop is tuned to a single frequency within the band of interest).

To minimize this issue, another embodiment illustrated in FIGS. 15A and 15B uses an un-tuned loop with a high input impedance at the receiver. FIG. 15A illustrates a loop terminated into a receiver with a high input impedance and FIG. 15B illustrates its equivalent circuit. In this aspect, the input impedance at the receiver is selected so that the energy lost due to the loop impedance, $L_1$, is relatively insignificant. Using Zin as the input impedance at the receiver, the voltage at the receiver, $V_1$, is calculated as shown below.

$$V_1 = V_s \frac{Zin}{Zin + j\omega L_1} \qquad \text{Equation 3}$$

Since Zin is much larger than $j\omega L_1$, this can be approximated by the following equation $$V_1 = V_s \frac{\infty}{\infty + j\omega L_1}, \text{ or } V_1 = V_s \qquad \text{Equation 4}$$

As shown by the foregoing equation, the use of a relatively high input impedance at the input of the receiver negates $L_1$ for all frequencies. In one embodiment, a high impedance buffer can be inserted between the loop and an exemplary 50 ohm receiver circuit. In this embodiment, the high impedance buffer is on the order of 1 Mohm while the impedance of the loop is on the order of 200 ohms. In other embodiments, it is contemplated that the input impedance is at least two times the loop impedance.

Figure 16:
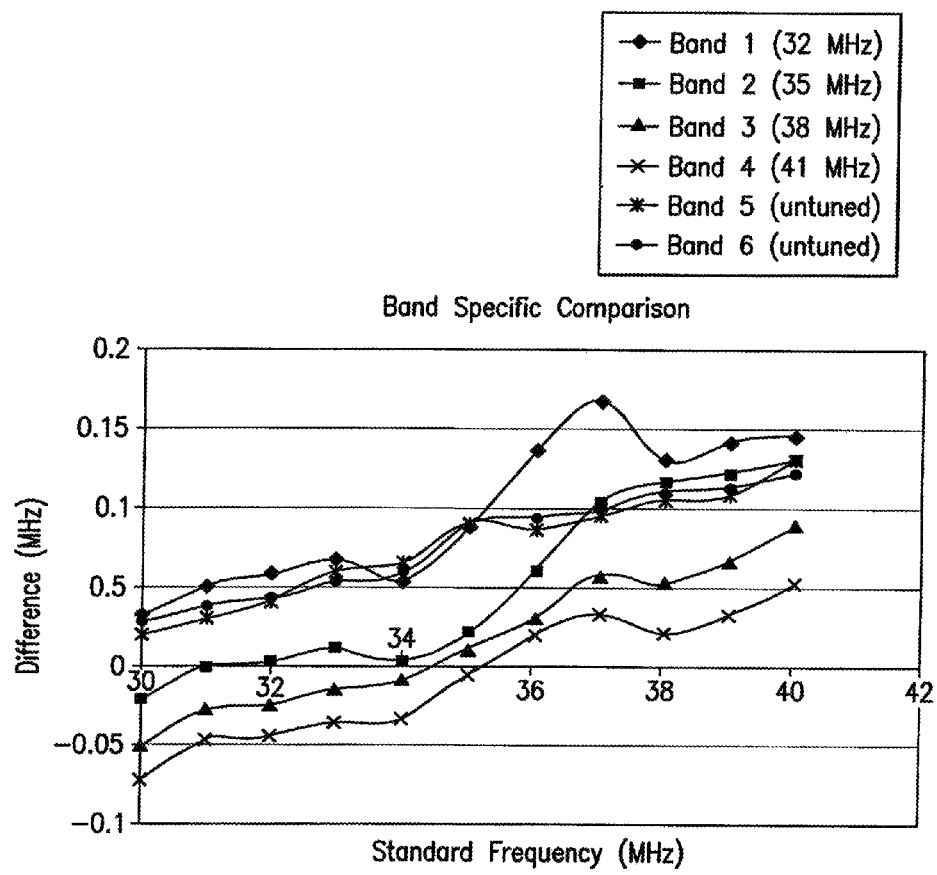
FIG. 16 is a graph that illustrates the comparison of the frequency response for tuned loops and the frequency response for un-tuned loops with high input impedances at the receiver.

In one aspect, the frequency response within the band of interest is more monotonic if the pressure sensor coupling loop uses a high input impedance at the receiver, than if a tuned loop is used with a 50 ohm input impedance. FIG. 16 compares the frequency response for tuned loops and the frequency response for un-tuned loops with high input impedances at the receiver. The y-axis represents the difference in measured frequency between a calibration system using a network analyzer and the loop. The x-axis represents the frequency of the L-C standard used in the measurements. Linear interpolation can be used between measurement points. Band 1 corresponds to a loop resonant at 32 MHz, Band 2 corresponds to a loop resonant at 35 MHz, Band 3 corresponds to a loop resonant at 38 MHz, and Band 4 corresponds to a loop resonant at 41 MHz. Bands 1-4 correspond to a prior art design that uses switched capacitors banks to vary the loop resonance to achieve the needed bandwidth. Bands 5 and 6 correspond to un-tuned loops.

Bands 1-4 illustrate a slope variation within the band of interest, which can affect the accuracy of measurements made using the loop. Bands 5 and 6 illustrate that the variation within the band of interest is less than in the systems using a tuned loop. The more monotonic frequency response of an un-tuned loop with a high input impedance generally requires a simpler set of calibration coefficients to be used for the frequency conversion calculation.

An alternative embodiment to using an un-tuned loop and a high input impedance is to use stagger-tuned loops. If stagger tuned loops are used to receive the output signal, then the loops can be tuned in a manner similar to that described in the following paragraphs in connection with the transmission of an energizing signal.

During the energizing mode, the energizing loop produces a magnetic field. The intensity of the magnetic field produced by the energizing loop depends, in part, on the magnitude of the current within the loop. In one aspect, the current is maximized at the energizing frequency if the impedance of the loop is essentially 0 ohms at the energizing frequency. The resonant frequency of the loop is related to the loop inductance and capacitance, as shown below.

$$f_o = \frac{1}{2\pi\sqrt{L*C1}} \qquad \text{Equation 5}$$

The impedance of the loop is preferably 0 ohms over the frequency range of interest, which, in an exemplary operating environment, can be, without limitation between about 30 MHz to about 37.5 MHz. To achieve the desired impedance over the desired frequency range, two or more loops can be stagger tuned as exemplarily shown in FIG. 17.

Figure 17:
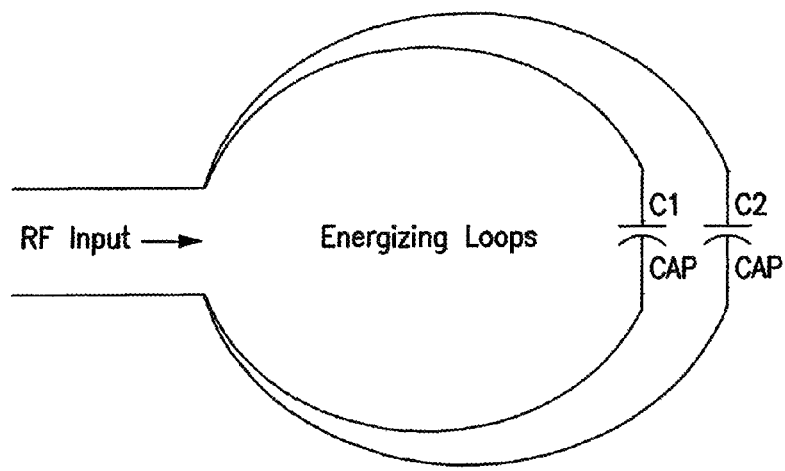
FIG. 17 schematically illustrated two stagger tuned loops.

The resonant frequencies for the loops are based on the bandwidth of interest. If there are two loops, then the loops can be spaced geometrically. In one exemplary non-limiting aspect, the resonant frequency of the first loop is can be about 31 MHz and the resonant frequency of the second loop can be about 36.3 MHz, which corresponds to the pole locations of a second order Butterworth bandpass filter having about −3 dB points at about 30 MHz and about 37.5 MHz. Although FIG. 17 illustrates two loops, it is contemplated that other embodiments can use a different number of loops, which provides coverage for a much wider frequency range. In one aspect, the loops can be spaced logarithmically if there are more than two loops.

Figure 18:
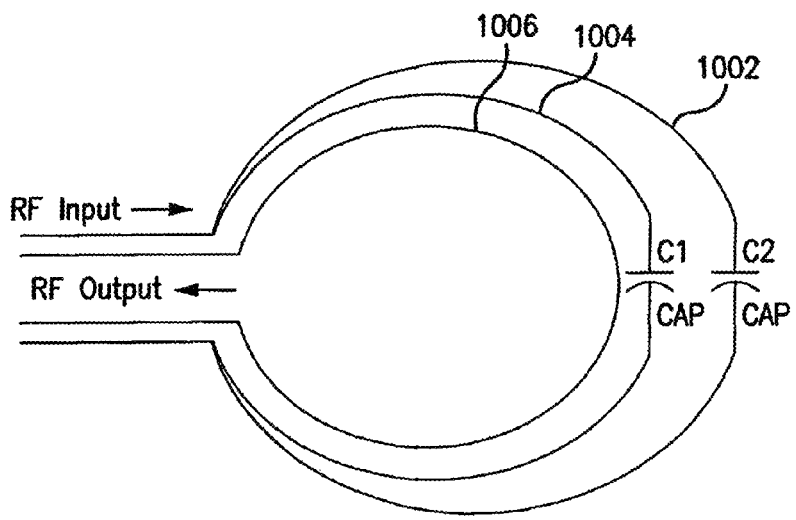
FIG. 18 illustrates the assembly of two stagger-tuned loops 1002, 1004 for transmitting the energizing signal to the passive electrical resonant circuit of the assembly and one un-tuned loop 1006 for receiving the output signal.

FIG. 18 illustrates the assembly of two stagger-tuned loops 1002, 1004 for transmitting the energizing signal to the passive electrical resonant circuit 80 of the t least one pressure sensor 60 and one un-tuned loop 1006 for receiving the output signal. In this aspect, the loops are parallel to one another with the un-tuned loop inside the stagger-tuned loops. Placing the loop used to receive the output signal inside of the loops used to transmit the energizing signal helps to shield the output signal from environmental interferences. In one embodiment, the loops can be positioned within a housing.

One will appreciate that the signal from an implanted passive pressure sensor is relatively weak and is attenuated by the surrounding tissue and the distance between the pressure sensor and the coupling loop. Optimizing the position and angle of the coupling loop relative to the pressure sensor can help maximize the coupling between the pressure sensor and the coupling loop. In one aspect, the coupling loop can be positioned so that a plane defined by the pressure sensor coupling loop is approximately parallel to the inductor within the passive electrical resonant circuit of the pressure sensor and the pressure sensor is approximately centered within the sensor coupling loop.

In one aspect, isolation of the energizing signal and the output signal provided by the base unit and the coupling loop can be maintained in the cable that connects the base unit to the coupling loop. In one aspect, a cable can connect the base unit to the coupling loop and isolate the energizing signal from the output signal. In one aspect, the distal end of the cable that connects to the base unit can comprise a multi-pin connector (e.g., AL06F15-ACS provided by Amphenol) and a right angle housing. The proximal end of the cable that connects to the coupling loop can comprise a first connector, which can be a multi-pin connector (e.g., AMP 1-87631-0 provided by Amphenol) that operably connects to the filtering and switching circuitry associated with the loop; a second connector that operably connects to the energizing loop; and a third connector that operably connects to the loop that couples the signal from the sensor. In this exemplary aspect, the right angle housing and the strain relief provide strain relief at the respective ends of the cable. When assembled with the housing, the strain relief can be positioned proximate to the housing. Optionally, other types of strain relief can be implemented, including, without limitation, physical constraints, such as tie wraps, ferrals or epoxy, and/or service loops. In one aspect, the cable can also comprise ferrite beads, which can help reduce ground currents within the cable.

In one aspect, the position of the coaxial cables within the cable is designed to maximize the isolation between the energizing signal and the sensor signal, while minimizing the diameter of the cable. The cable is configured to maximize the isolation between the coax cable that transmits the energizing signal and the inner bundle and the twisted pairs and the coax cable that receives the sensor signal and the inner bundle.

In an alternative embodiment and referring now to FIGS. 19(a)-26, the interrogation system can be configured to determine the resonant frequency of the pressure sensor (and therefore the desired pressure) by adjusting the phase and frequency of an energizing signal until the frequency of this signal locks to the resonant frequency of the pressure sensor. In one aspect, the interrogation system energizes the pressure sensor with a low duty cycle, gated burst of RF energy of a predetermined frequency or set of frequencies and predetermined amplitude. This signal induces a current in the pressure sensor that can be used to track the resonant frequency of the pressure sensor. The interrogation system receives the ring down response of the pressure sensor and determines the resonant frequency of the pressure sensor, which is used to calculate the pressure acting thereon the pressure sensor. As described above, interrogation the system can use a pair of PLL's to adjust the phase and the frequency of the energizing signal to track the resonant frequency of the pressure sensor.

Optionally, the interrogation system can be used in two environments: 1) the operating room during implantation and 2) the doctor's office during follow-up examinations. It is contemplated that during implantation, the interrogation system can be used to record at least two measurements. The first measurement can be taken during introduction of the pressure sensor for calibration and the second measurement can be taken after placement for functional verification of the stent.

The interrogation system communicates with the implanted pressure sensor to determine the resonant frequency of the pressure sensor, which comprises an LC resonant circuit having a variable capacitor. In this aspect, the distance between the plates of the variable capacitor varies as the surrounding pressure varies. Thus, the resonant frequency of the circuit can be used to determine the pressure acting thereon the pressure sensor.

In one aspect, the interrogation system can energize the pressure sensor with an RF burst. The energizing signal can be a low duty cycle, gated burst of RF energy of a predetermined frequency or set of frequencies and a predetermined amplitude. In one non-limiting example, the duty cycle of the energizing signal can range between about 0.1% to 50%. In another non-limiting example, the interrogation system can energize the pressure sensor with a 30-37.5 MHz fundamental signal at a pulse repetition rate of 100 kHz with a duty cycle of 20%. The energizing signal is coupled to the pressure sensor via a magnetic loop. This signal induces a current in the pressure sensor which has maximum amplitude at the resonant frequency of the pressure sensor. During this time, the pressure sensor charges exponentially to a steady-state amplitude that is proportional to the coupling efficiency distance between the pressure sensor and loop, and the RF power.

Figure 24:
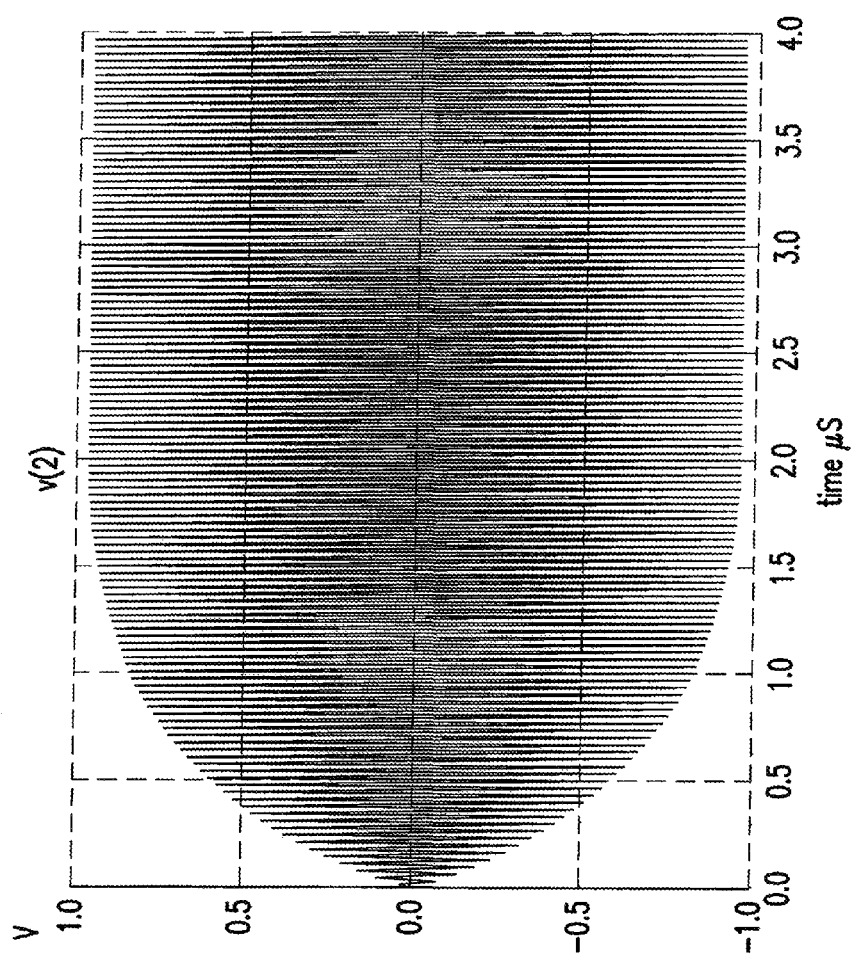
FIG. 24 is a graph illustrating an exemplary charging response of an LC circuit.

FIG. 24 shows the charging response of a typical LC circuit to a burst of RF energy at its resonant frequency. The speed at which the pressure sensor charges is directly related to the Q (quality factor) of the pressure sensor. Therefore, the "on time" of the pulse repetition duty cycle is optimized for the Q of the pressure sensor. The system receives the ring down response of the pressure sensor via magnetic coupling and determines the resonant frequency of the pressure sensor.

Figure 19A:
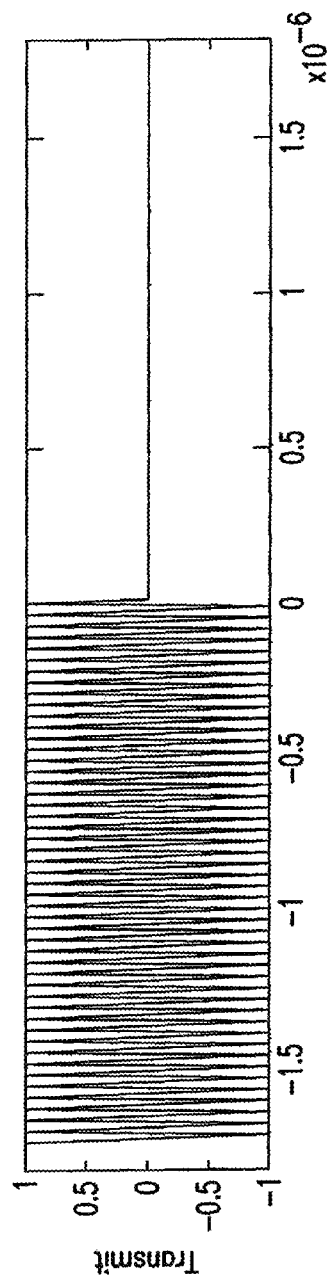
FIG. 19(*a*) is a graph illustrating an exemplary energizing signal.
Figure 19B:
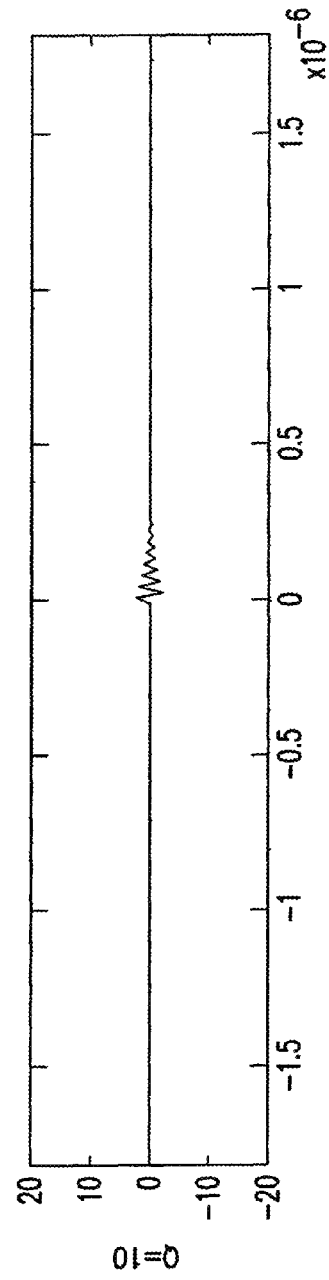
Figure 19C:
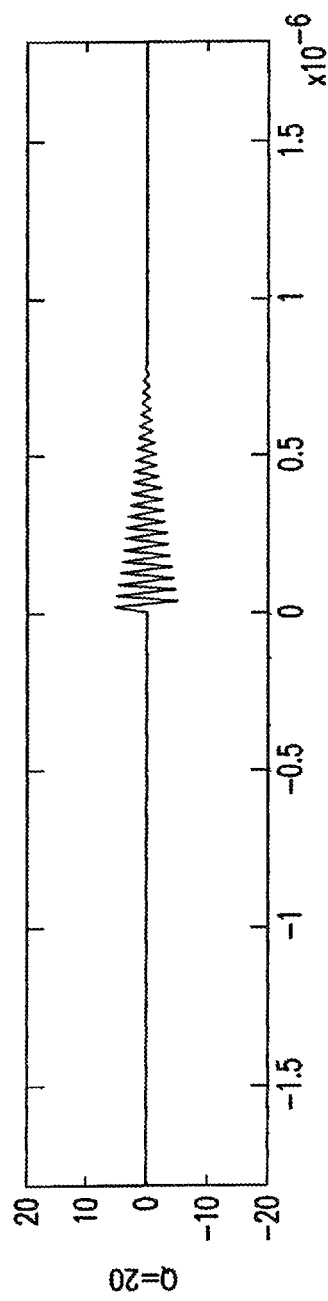
Figure 19D:
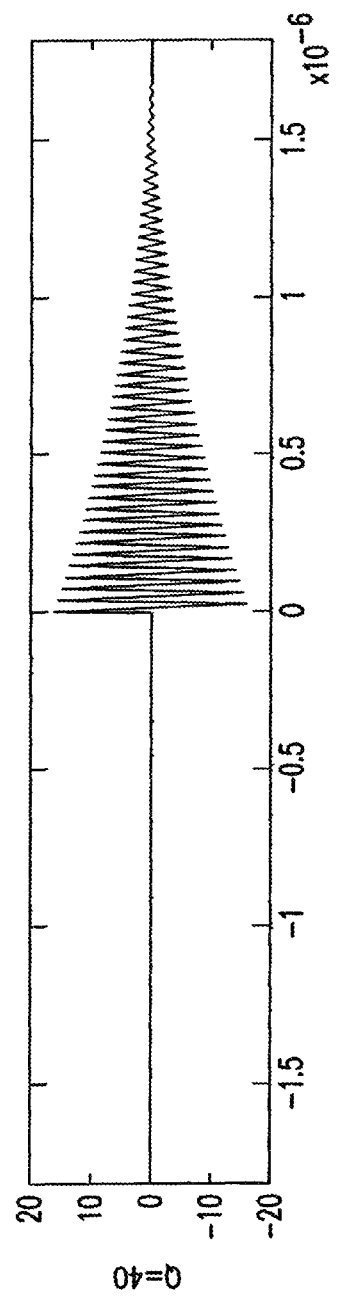

FIG. 19(a) illustrates a typical energizing signal and FIGS. 19(b), 19(c) and 19(d) illustrate typical coupled signals for various values of Q (quality factor) for the pressure sensor. When the main unit is coupling energy at or near the resonant frequency of the pressure sensor, the amplitude of the pressure sensor return is maximized, and the phase of the pressure sensor return will be close to zero degrees with respect to the energizing phase. The pressure sensor return signal is processed via phase-locked-loops to steer the frequency and phase of the next energizing pulse.

Figure 20:
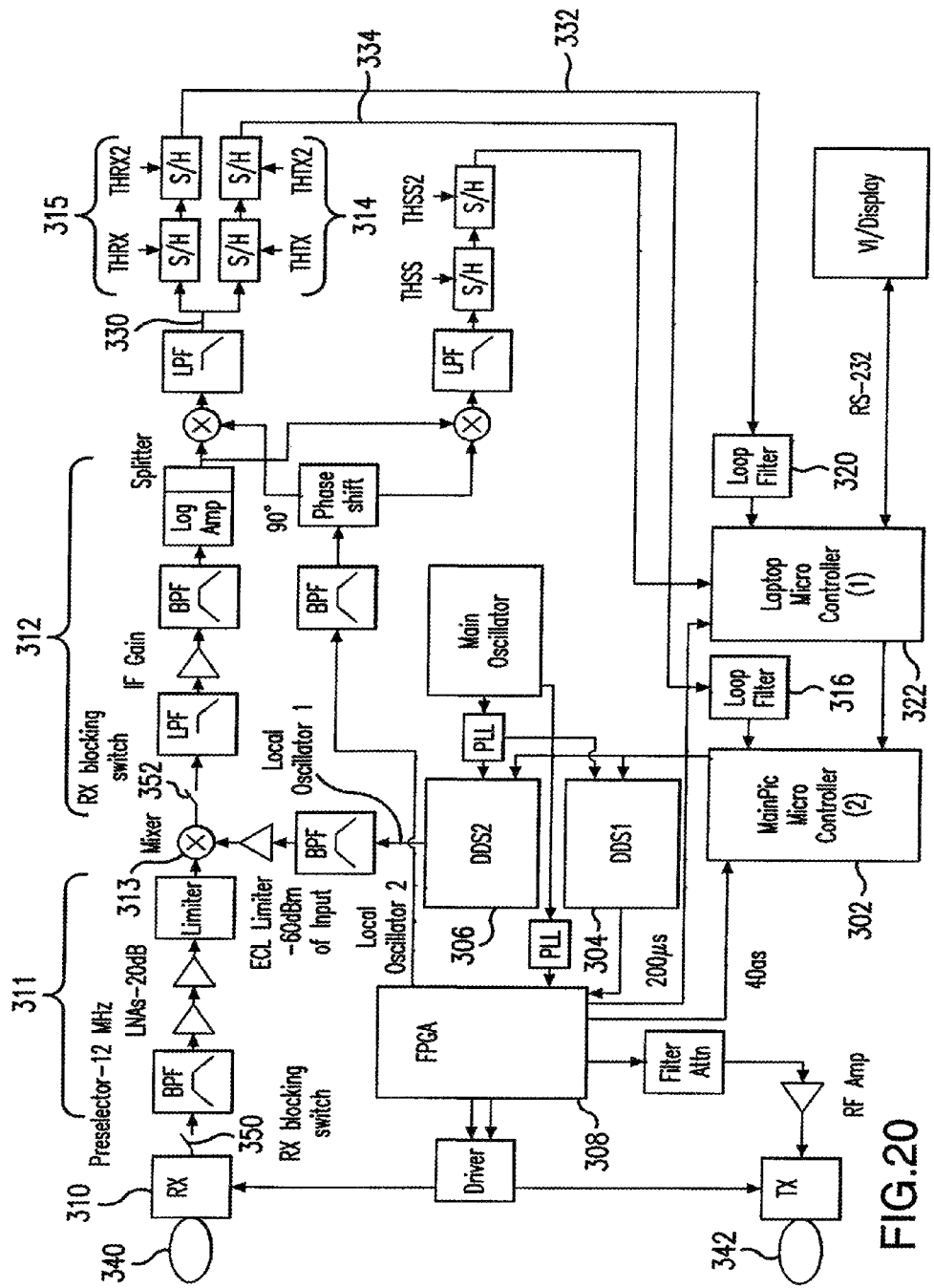
FIG. 20 is a schematic block diagram of an exemplary base unit of an interrogation system.

In a further aspect, FIG. 20 illustrates a schematic diagram of the signal processing components within an exemplary base unit 102. In one aspect, the base unit determines the resonant frequency of the pressure sensor by adjusting the energizing signal so that the frequency of the energizing signal matches the resonant frequency of the pressure sensor. In the exemplary embodiment illustrated by FIG. 20, two separate processors 302, 322 and two separate coupling loops 340, 342 are shown. In one embodiment, processor 302 is associated with the base unit and processor 322 is associated with a computer connected to the base unit. In other embodiments, it is contemplated that a single processor can be used to provide the same functions as the two separate processors. In other embodiments, it is also contemplated that a single loop can be used for both energizing and for coupling the pressure sensor energy back to the receiver. As will be apparent to those skilled in the art, other configurations of the base unit are possible that use different components.

In one aspect, a pair of PLLs can be used. Is this aspect, the fast PPL is used to adjust the phase of the energizing signal and the slow PLL is used to adjust the frequency of the energizing signal. The base unit 102 can be configured to provide two cycles: the calibration cycle and the measurement cycle. In one aspect, the first cycle is a 10 microsecond energizing period for calibration of the system, which is referred to herein as the calibration cycle, and the second cycle is a 10 microsecond energizing/coupling period for energizing the pressure sensor and coupling a return signal from the pressure sensor, which is referred to herein as the measurement cycle.

During the calibration cycle, the interrogation system generates a calibration signal for system and environmental phase calibration and during the measurement cycle the system both sends and listens for a return signal, i.e. the pressure sensor ring down. Alternatively, as those skilled in the art will appreciate, the calibration cycle and the measurement cycle can be implemented in the same pulse repetition period.

The phase of the energizing signal is adjusted during the calibration cycle by the fast PLL and the frequency of the energizing signal is adjusted during the measurement cycle by the slow PLL. The following description of the operation of the PLLs is presented sequentially for simplicity. However, as those skilled in the art will appreciate, the PLLs can operate simultaneously.

Initially the frequency of the energizing signal is set to a default value determined by the calibration parameters of the at least one pressure sensor. Each pressure sensor is associated with a number of calibration parameters, such as frequency, offset, and slope. An operator of the interrogation system enters the pressure sensor calibration parameters into the interrogation system via the user interface and the interrogation system determines an initial frequency for the energizing signal based on the particular pressure sensor. Alternatively, the pressure sensor calibration information could be stored on portable storage devices, bar codes, or incorporated within a signal returned from the pressure sensor. In one aspect, the initial phase of the energizing signal can be arbitrary.

The initial frequency and the initial phase are communicated from the processor 302 to the DDSs (direct digital synthesizers) 304, 306. The output of DDS1 304 is set to the initial frequency and initial phase and the output of DDS2 306 (also referred to as local oscillator 1) is set to the initial frequency plus the frequency of the local oscillator 2. In one aspect, the phase of DDS2 is a fixed constant. In one embodiment, the frequency of local oscillator 2 is 4.725 MHz. The output of DDS 1 is gated by the field programmable gate array (FPGA) 308 to create a pulsed transmit signal having a pulse repetition frequency ("PRF"). The FPGA provides precise gating so that the base unit can sample the receive signal during specific intervals relative to the beginning or end of the calibration cycle.

During the calibration cycle, the calibration signal which enters the receiver 310 is processed through the receive section 311 and the IF section 312, and is sampled. In one embodiment, the calibration signal is the portion of the energizing signal that leaks into the receiver (referred to herein as the energizing leakage signal). The signal is sampled during the on time of the energizing signal by a sample and hold circuit 314 to determine the phase difference between the signal and local oscillator 2. FIG. 20 illustrates two cascaded sample and holds in circuit 314 to provide both fast sampling and a long hold time. Alternatively, a single sample and hold can be used in circuit 314. In the embodiment where the calibration signal is the portion of the energizing signal that leaks into the receiver, the signal is sampled approximately 100 ns after the beginning of the energizing signal pulse. Since the energizing signal is several orders of magnitude greater than the coupled signal, it is assumed that the phase information associated with the leaked signal is due to the energizing signal and the phase delay is due to the circuit elements in the coupling loop, circuit elements in the receiver, and environmental conditions, such as proximity of reflecting objects.

The phase difference is sent to a loop filter 316. The loop filter is set for the dynamic response of the fast PLL. In one embodiment, the PLL bandwidth is 1000 Hz and the damping ratio is 0.7. A DC offset is added to allow for positive and negative changes. The processor 302 reads its analog to digital converter (A/D) port to receive the phase difference information and adjusts the phase sent to direct digital synthesizer 1 (DDS 1) to drive the phase difference to zero. This process is repeated alternatively until the phase difference is zero or another reference phase.

The phase adjustment made during the energizing period acts to zero the phase of the energizing signal with respect to local oscillator 2. Changes in the environment of the antenna or the receive chain impedance, as well as the phase delay within the circuitry prior to sampling affect the phase difference reading and are accommodated by the phase adjustment.

During the measurement cycle, the energizing signal may be blocked from the receiver during the on time of the energizing signal. During the off time of the energizing signal, the receiver is unblocked and the coupled signal from the pressure sensor is received. The coupled signal is amplified and filtered through the receive section 311. The signal is down converted and additional amplification and filtering takes place in the IF section 312. In one embodiment, the signal is down converted to 4.725 MHz. After being processed through the IF section, the signal is mixed with local oscillator 2 and sampled by sample and hold circuits 315 to determine the phase difference between the coupled signal and the energizing signal. FIG. 20 illustrates two cascaded sample and holds in circuit 315 to provide both fast sampling and a long hold time. Alternatively, a single sample and hold can be used in circuit 315. In one embodiment, the sampling occurs approximately 30 ns after the energizing signal is turned off.

In other aspects, group delay or signal amplitude can be used to determine the resonant frequency of the pressure sensor. The phase curve of a second order system passes through zero at the resonant frequency. Since the group delay (i.e. the derivative of the phase curve) reaches a maximum at the resonant frequency, the group delay can be used to determine the resonant frequency. Alternatively, the amplitude of the pressure sensor signal can be used to determine the resonant frequency. The pressure sensor acts like a bandpass filter so that the pressure sensor signal reaches a maximum at the resonant frequency.

The sampled signal is accumulated within a loop filter 320. The loop filter is set for the dynamic response of the slow PLL to aid in the acquisition of a lock by the slow PLL. The PLLs are implemented with op-amp low pass filters that feed A/D inputs on microcontrollers, 302 and 322, which in turn talk to the DDSs, 304 and 306, which provide the energizing signal and local oscillator 1. The microcontroller that controls the energizing DDS 304 also handles communication with the display. The response of the slow PLL depends upon whether the loop is locked or not. If the loop is unlocked, then the bandwidth is increased so that the loop will lock quickly. In one embodiment, the slow PLL has a damping ratio of 0.7 and a bandwidth of 120 Hz when locked (the Nyquist frequency of the blood pressure waveform), which is approximately ten times slower than the fast PLL.

A DC offset is also added to the signal to allow both a positive and a negative swing. The output of the loop filter is input to an A/D input of processor 322. The processor determines a new frequency and sends the new frequency to the DSSs. The processor offsets the current frequency value of the energizing signal by an amount that is proportional to the amount needed to drive the output of the slow PLL loop filter to a preset value. In one embodiment the preset value is 2.5V and zero in phase. The proportional amount is determined by the PLL's overall transfer function.

The frequency of the energizing signal is deemed to match the resonant frequency of the pressure sensor when the slow PLL is locked. Once the resonant frequency is determined, the pressure can be calculated using the calibration parameters associated with the respective pressure sensor, which results in a difference frequency that is proportional to the measured pressure.

The operation of the slow PLL is qualified based on signal strength. The base unit includes signal strength detection circuitry. If the received signal does not meet a predetermined signal strength threshold, then the slow PLL is not allowed to lock and the bandwidth and search window for the PLL are expanded. Once the received signal meets the predetermined signal strength threshold, then the bandwidth and search window of the slow PLL is narrowed and the PLL can lock.

In one aspect, phase detection and signal strength determination can be provided via the "I" (in phase) and "Q" (quadrature) channels of a quadrature mixer circuit. The "I" channel is lowpass filtered and sampled to provide signal strength information to the processing circuitry. The "Q" channel is lowpass filtered and sampled (THSS, THSS2) to provide phase error information to the slow PLL.

The base unit can comprise two switches, RX blocking switches 350 and 352, that aid in the detection of the pressure sensor signal. One of the RX blocking switches precedes the preselector in the receive section 311 and the other RX blocking switch follows the mixer in the IF section 312. The FPGA controls the timing of the RX blocking switches (control signals not shown). The RX blocking switches are closed during the on time of the energizing signal during the calibration cycle and generally closed during the off time of the energizing signal during the measurement cycle. During the measurement cycle the timing of the RX blocking switches is similar to the timing of the switch that controls the energizing signal into the receiver during the measurement cycle, but the RX blocking switches are closed slightly later to account for signal travel delays in the system. The RX blocking switches prevent the energizing signal that leaks into the receiver during the measurement cycle (specifically during the on time of the energizing signal) from entering the IF section. If the leakage signal enters the IF section, then it charges the IF section and the IF section may not settle out before the pressure sensor signal arrives. For example, in one instance the IF section was charged for several hundred nanoseconds after the on time of the energizing signal. Blocking the leakage signal from the IF section eliminates this problem and improves detection of the pressure sensor signal.

In another embodiment, the base unit can be configured to use multiple sampling points rather than the single sampling point discussed above in connection with FIG. 20. If a single sampling point is used and the sampling point coincides with a point where the average DC voltage of the phase detector is zero, then the system can lock even though the frequency is not the correct frequency. This situation can occur when there is system stress, such as a DC offset in the loop integrator or some other disturbance. The use of multiple sampling points helps prevent a false lock under these circumstances.

Figure 25:
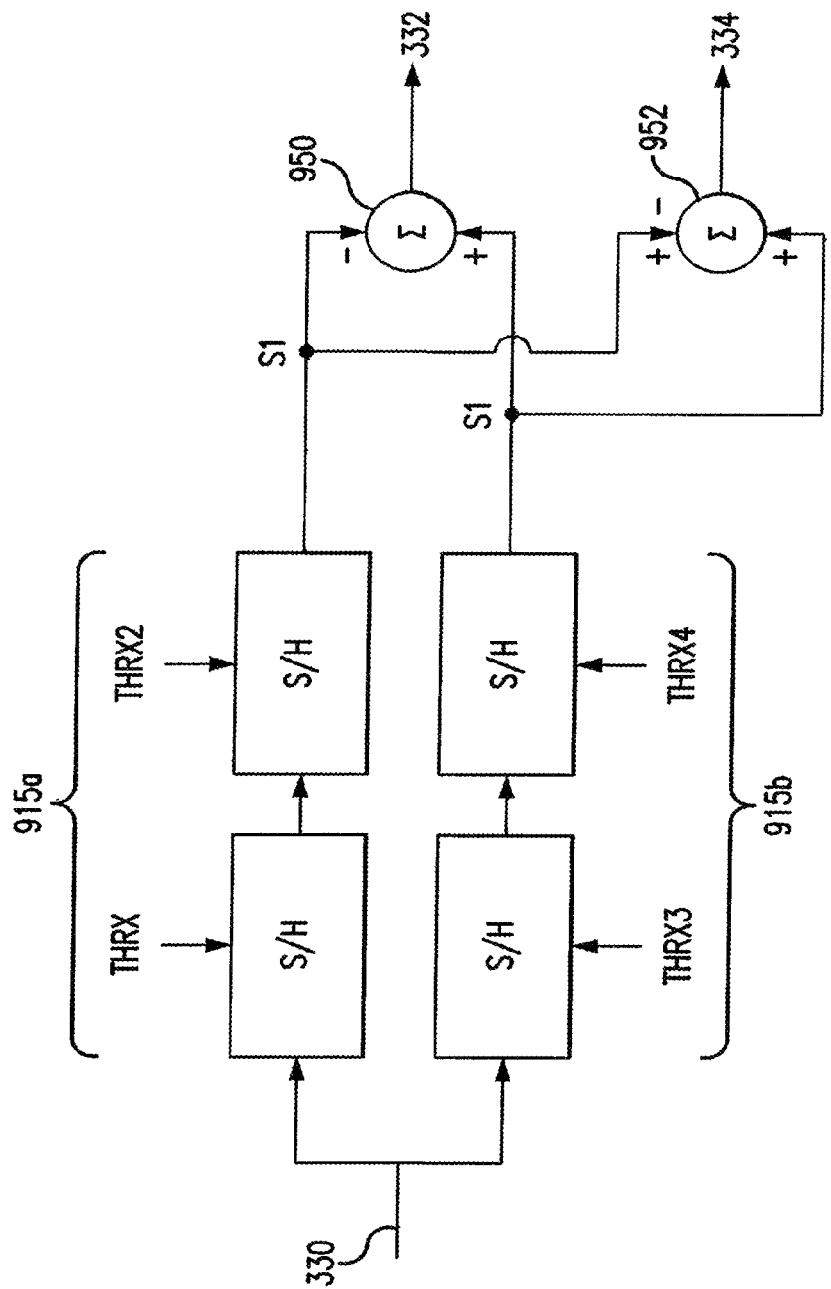
FIG. 25 is a partial schematic block diagram of a portion of an embodiment of an exemplary base unit of an interrogation system.

FIG. 25 illustrates a portion of the base unit for an embodiment that uses two sampling points, S1, S2. In this aspect, the components illustrated in FIG. 25 are used instead of the sample and hold components 314, 315 used in FIG. 20. As discussed above in connection with FIG. 20, this embodiment uses a pair of PLLs. The phase of the energizing signal is adjusted by the fast PLL and the frequency of the energizing signal is adjusted by the slow PLL. However, in this embodiment only a single cycle is needed to adjust the phase and frequency of the energizing signal, i.e. separate calibration and measurement cycles are not necessary. Since only a single cycle is used, the timing of the RX blocking switches is slightly different than that described above in connection with FIG. 20. In this embodiment, the RX blocking switches are generally closed during the off time of the energizing signal. The specific timing of the closure of the RX blocking switches may be system specific and can be adjusted to account for signal travel delays in the system.

The initial frequency and phase of the energizing signal are set as described above in connection with FIG. 20. The energizing signal may be blocked from the receiver during the on time of the energizing signal. During the off time of the energizing signal, the receiver is unblocked and the coupled signal from the pressure sensor is received. The coupled signal is amplified and filtered through the receive section 311. The signal is down converted and additional amplification and filtering takes place in the IF section 312. In one aspect, the signal is down converted to 4.725 MHz. After being processed through the IF section, the signal is mixed with local oscillator 2 and sampled by the two sample and hold circuits 915a and 915b to determine the phase difference between the coupled signal and the energizing signal.

The two sample points are applied to a first differential amplifier 950 and a second differential amplifier 952. The first differential amplifier outputs a signal representing the difference between the two sampling points (S2-S1), which is fed into the loop filter 320 and used to adjust the frequency of the energizing signal. The second differential amplifier 952 outputs a signal representing the sum of the two sampling points (S1+S2), which is fed into the loop filter 316 and used to adjust the phase of the energizing signal.

In this aspect, the FPGA controls the timing of the two sample and hold circuits. In one aspect, the first sample point occurs approximately 30 ns after the energizing signal is turned off and the second sample point occurs approximately 100 to 150 ns after the energizing signal is turned off. The timing of the first sampling point can be selected so that the first sampling point occurs soon after the switching and filter transients have settled out. The timing of the second sampling point can be selected so that there is sufficient time between the first sampling point and the second sampling point to detect a slope, but before the signal becomes too noisy.

The frequency of the energizing signal is deemed to match the resonant frequency of the pressure sensor when the slow PLL is locked. Once the resonant frequency is determined, the pressure is calculated using the calibration parameters associated with the pressure sensor, which results in a difference frequency that is proportional to the measured pressure.

In yet another aspect, the base unit can use continuous signal processing techniques instead of the sampled processing techniques discussed above in connection with FIGS. 20 and 25. This embodiment derives continuous wave signals from the pulsed calibration signal and the pulsed pressure sensor signal and uses the continuous wave signals to adjust the phase and frequency of the energizing signal.

Figure 26:
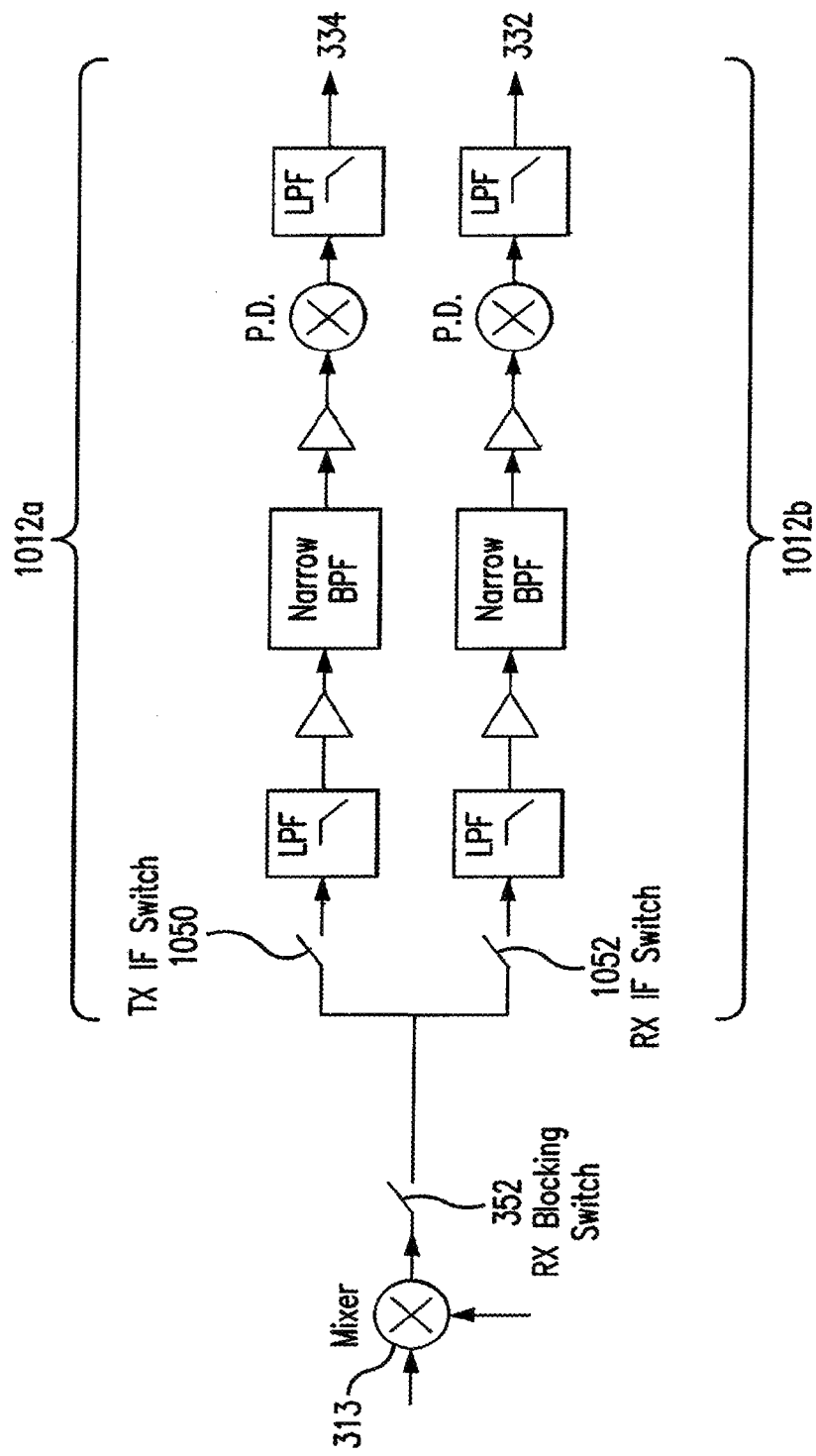
FIG. 26 is a partial schematic block diagram of a portion of an embodiment of an exemplary base unit of an interrogation system.

FIG. 26 illustrates a portion of the base unit for an embodiment that uses continuous signal processing. In this aspect, separate calibration 1012a and measurement sections 1012b can be used instead of the common IF section 312 and separate sample and hold circuits 314 and 315 used in FIG. 20. In one aspect, after the signal passes through the receiver section 311, the mixer, and one of the RX blocking switches, the signal is split into a pair of switches, TX IF switch 1050 and RX IF switch 1052. The FPGA controls the switches (control signals not shown) so that the TX IF switch 1050 is closed and the RX IF switch 1052 is opened during the calibration cycle and the TX IF switch is opened and the RX IF switch is closed during the measurement cycle. The calibration section 1012a and the measurement section 1012b can each include the aforementioned switch, a low pass filter, a narrow bandpass filter, amplifiers and a phase detector. The common IF section of FIG. 20 can use a bandpass filter, typically on the order of 2-3 MHz, whereas the calibration and measurements sections of FIG. 26 can use a narrow bandpass filter, typically on the order of 60-120 kHz.

In one aspect, it is contemplated that the system illustrated by FIG. 26 can use alternating calibration and measurement cycles. However, it is also contemplated that the calibration cycle and the measurement cycle can be implemented in the same pulse repetition period.

During the calibration cycle, the calibration signal which enters the receiver 310 is processed through the receive section 311 and the calibration section 1012a. The phase difference output from the calibration section is sent to the loop filter 316 and the adjustment of the phase of the energizing signal proceeds as described above in connection with FIG. 20.

During the measurement cycle, the energizing signal can be blocked from the receiver during the on time of the energizing signal. During the off time of the energizing signal, the receiver is unblocked and the pressure sensor signal is received. The coupled signal is amplified and filtered through the receive section 311 and then transferred to the measurement section 1012b. The phase difference output from the measurement section is sent to loop filter 320 and the adjustment of the frequency of the energizing signal proceeds as described above in connection with FIG. 20.

In one aspect, the RX blocking switches close as described above in connection with FIG. 20, but open earlier during the measurement cycle. Instead of being closed through the end of the off time of the energizing signal, the RX blocking switches open before the end of the off time. The timing of the opening of the RX blocking switches is based on the pressure sensor characteristics and is selected so that the switches open once the pressure sensor signal falls below the noise level. Since most of the energy from pressure sensor signal is received within a time period of Q/fo, where Q is the Q of the pressure sensor and fo is the center frequency of the pressure sensor, the RX blocking switches can be opened after approximately Q/fo. For example, if the Q of the pressure sensor if 40 and the fo is 32 MHz, then the RX blocking switches are opened after approximately 1.25 microseconds during the measurement cycle. The Q of the pressure sensor and an approximate fo of the pressure sensor are typically known and can be used to control the timing of the RX blocking switches.

The sampled information is used when utilizing the sample and hold techniques and the noise after the sample point(s) is ignored. However, in this continuous signal embodiment, all of the noise is seen unless other adjustments are made. Opening the RX blocking switches once the pressure sensor signal decays below the noise level helps reduce the noise seen by the rest of the system and improves detection of the pressure sensor signal.

The frequency spectrum of the pressure sensor signal includes a number of spectral components that correspond to the pulse repetition frequency, including a strong component corresponding to the center frequency of the energizing signal (fo). The information needed to determine the resonant frequency of the pressure sensor can be obtained by examining the phase of the spectral component that corresponds to fo. The measurement section isolates the spectral component at fo and the resulting time domain signal is a continuous wave signal.

In various aspects, the interrogation system generates an energizing signal with a random or pseudo random frame width. For example, the pulse width can be 2 microseconds for each frame, but the frame size can be pseudo randomly selected from a plurality of possible frame sizes, such as, for example and without limitation, 6.22 microseconds, 8.76 microseconds, 11.30 microseconds and 13.84 microseconds. It is contemplated that any number of frame sizes can be used, although at some point increasing the number of possible frame sizes can increase the interrogation system complexity with only incremental improvements.

In one aspect, the minimum frame sizes generally correspond to the smallest frame size that provides a sufficient receive window and typically corresponds to the pulse width. For example, and without limitation, if the pulse width is 2 microseconds, then the minimum receive window is also about 2 microseconds, which makes the minimum frame size about 4 microseconds. However, switching times and other practical considerations related to the components used may result in a slightly larger frame size. The maximum frame size is typically based on a desired average pulse repetition rate. In this example, if the average pulse repetition rate is selected as 10 microseconds, then the maximum frame size is about 14 microseconds.

If a random or pseudo random frame width is used, then the frame width can vary between the calibration cycle and the measurement cycle or a common frame width can be used for a calibration cycle and the following measurement cycle. The use of a random or pseudo random frame width helps isolate the spectral component needed to determine the resonant frequency of the pressure sensor and relaxes the requirements of the narrow bandpass filter used in the receive section.

Optionally, the RX blocking switch 352 can be combined with the TX IF switch 1050 and the RX IF switch 1052 and the control of the TX IF and the RX IF switches can be modified to accommodate the combination.

In another aspect, the interrogation system can be configured to minimize potential false lock problems. Typically, a false lock occurs if the interrogation system locks on a frequency that does not correspond to the resonant frequency of the pressure sensor. In one aspect, a false lock can arise due to the pulsed nature of the system. Since the energizing signal is a pulsed signal, it includes groups of frequencies. The frequency that corresponds to a false lock is influenced by the pulse repetition frequency, the Q of the pressure sensor, and the duty cycle of the RF burst. For example, a constant pulse repetition frequency adds spectral components to the return signal at harmonic intervals around the resonant frequency of the pressure sensor, which can cause a false lock. In one embodiment, false locks occur at approximately 600 kHz above and below the resonant frequency of the pressure sensor. To determine a false lock, the characteristics of the signal are examined. For example, pulse repetition frequency dithering and/or observing the slope of the baseband signal are two possible ways of determine a false lock. In one aspect where the system locks on a sideband frequency, the signal characteristics correspond to a heartbeat or a blood pressure waveform.

In another aspect, a false lock can arise due to a reflection or resonance of another object in the vicinity of the system. This type of false lock can be difficult to discern because it generally does not correspond to a heartbeat or blood pressure waveform. The lack of frequency modulation can be used to discriminate against this type of false lock. Changing the orientation of the magnetic loop can also affect this type of false lock because the reflected false lock is sensitive to the angle of incidence.

In yet another aspect, a false lock can arise due to switching transients caused by switching the PIN diodes and analog switches in the RF path. These transients cause damped resonances in the filters in the receive chain, which can appear similar to the pressure sensor signal. Typically, these types of false locks do not correspond to a heartbeat or blood pressure waveform because they are constant frequency. These types of false locks are also insensitive to orientation of the magnetic loop.

Figure 21A:
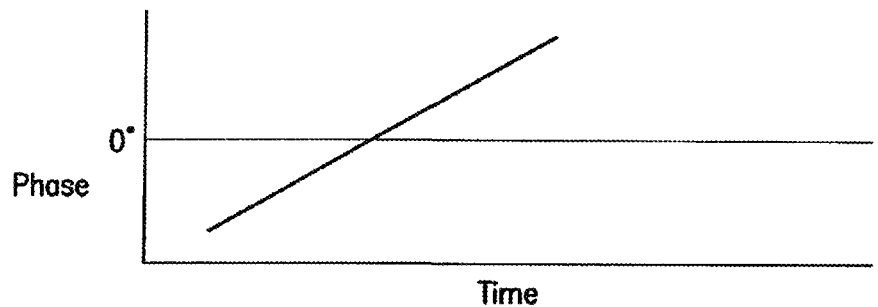
FIGS. 21(*a*) and 21(*b*) are graphs illustrating exemplary phase difference signals.
Figure 21B:
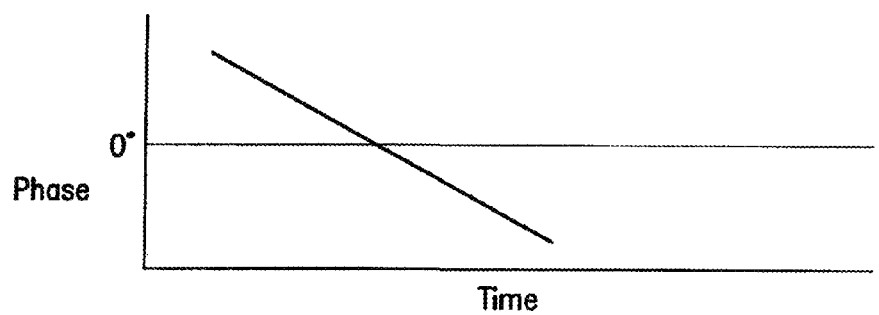

In one exemplary aspect, the interrogation system can be configured to prevent the occurrence of a false lock resulting from interrogation system locking on a frequency that does not correspond to the resonant frequency of the pressure sensor. In this aspect, to avoid the false lock, the interrogation system determines the slope of the baseband signal (the phase difference signal at point 330). In one aspect, if the slope is positive, then the lock is deemed a true lock. However, if the slope is negative, then the lock is deemed a false lock. In another embodiment, a negative slope is deemed a true lock and a positive slope is deemed a false lock. The slope is determined by looking at points before and after the phase difference signal goes to zero. The slope can be determined in a number of different ways, including but not limited to, using an analog differentiator or multiple sampling. FIGS. 21(a) and 21(b) illustrate a true lock and a false lock respectively, when a positive slope indicates a true lock.

In another aspect, if a false lock is detected, then the signal strength can be suppressed so that the signal strength appears to the processor 322 to be below the threshold and the system continues to search for the center frequency. In other aspect, any non-zero slope can be interpreted as a false lock resulting in zero signal strength.

Figure 5:
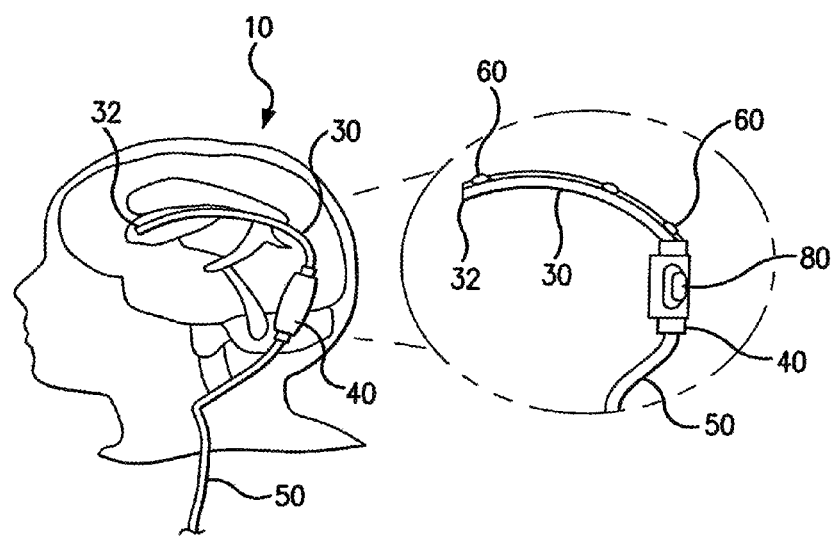
FIG. 5 is a schematic view of a ventricular shunt system in which a ventricular catheter is positioned in fluid communication with a ventricle of a brain of a subject and a drainage catheter is positioned in fluid communication with a remote body cavity. The ventricular catheter has a first pressure sensor mountable in a proximal portion of the ventricular catheter and a second pressure sensor mountable in a distal portion of the ventricular catheter. Each pressure sensor is electrically coupled to a portion of a passive electrical resonant circuit that is mountable thereon a portion of the ventricular shunt system.
Figure 6:
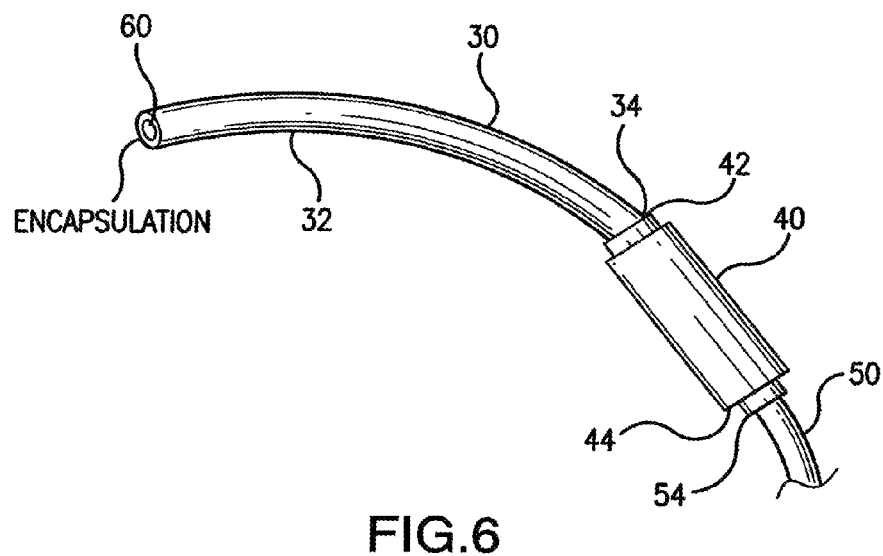
FIG. 6 is a schematic view of a ventricular shunt system in which a ventricular catheter is configured to be positioned in fluid communication with a ventricle of a brain of a subject and a drainage catheter is configured to be positioned in fluid communication with a remote body cavity and showing a pressure sensor encapsulated at the proximal end portion of the ventricular catheter.
Figure 7:
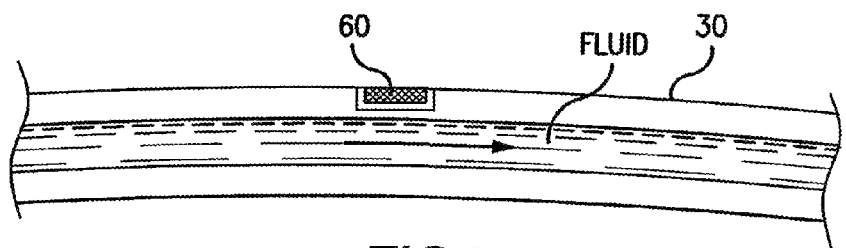
FIG. 7 is a schematic view of a ventricular shunt system in which a ventricular catheter is configured to be positioned in fluid communication with a ventricle of a brain of a subject and a drainage catheter is configured to be positioned in fluid communication with a remote body cavity and showing a pressure sensor connected to a portion of the wall of the ventricular catheter. Optionally, the sensor can be position in the outer portion or the inner portion of the wall as desired.
Figure 8:
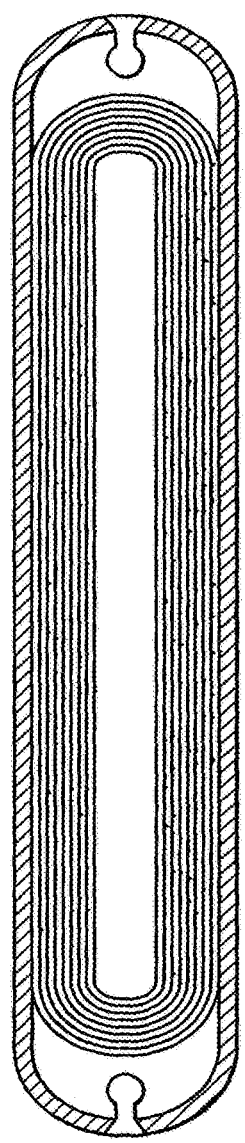
FIG. 8 schematically illustrates an exemplary substantially planar LC resonant circuit, which circuit is described in detail in commonly assigned U.S. patent application Ser. No. 12/175,803.
Figure 9:
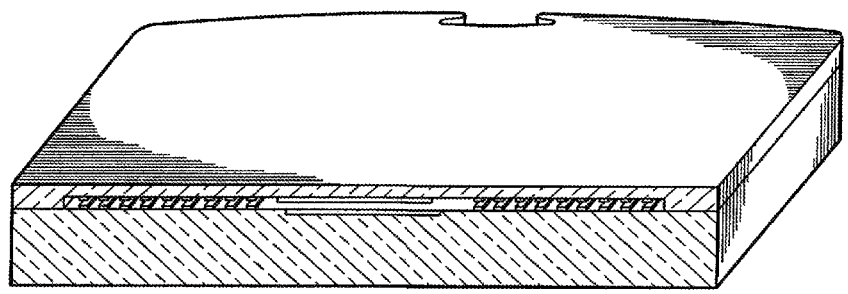
FIG. 9 is an exemplary cross-sectional perspective view of the LC resonant circuit of FIG. 8.
Figure 10:
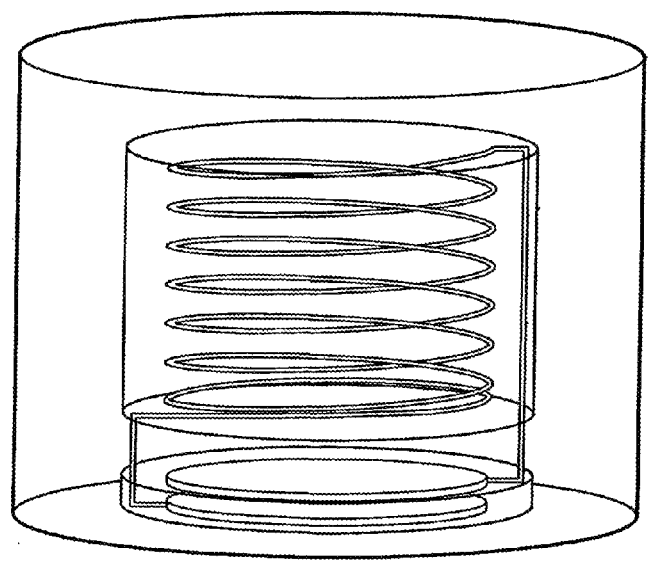
FIG. 10 schematically illustrates a coil inductor of an exemplary LC resonant circuit having a longitudinal axis, which circuit is described in detail in commonly assigned U.S. patent application Ser. No. 11/157,375.
Figure 22:
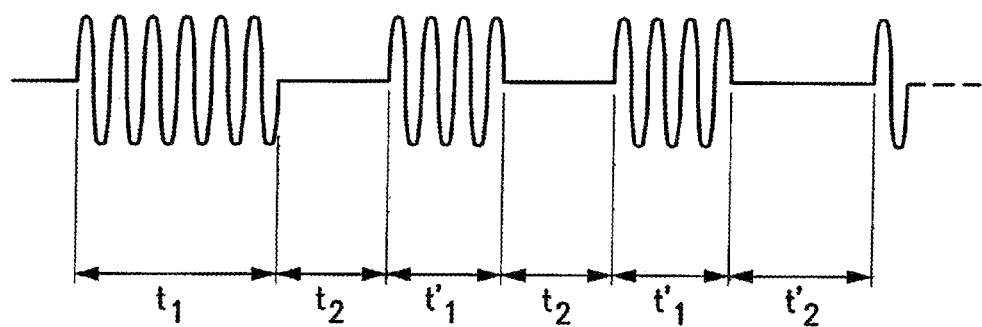
FIG. 22 illustrates frequency dithering.

In one aspect, the interrogation system can also use frequency dithering to avoid the occurrence of a false lock resulting from interrogation system locking on a frequency that does not correspond to the resonant frequency of the pressure sensor. In this aspect, since the spectral components associated with a constant pulse repetition frequency can cause a false lock, dithering the pulse repetition frequency helps avoid a false lock. By dithering the pulse repetition frequency, the spectral energy at the potential false lock frequencies is reduced over the averaged sampling interval. As shown in FIG. 22, the energizing signal includes an on time t1 and an off time t2. The system can vary the on time or the off time to vary the PRF (PRF=1/(t1+t2)). FIG. 5 illustrates different on times (t1, t1') and different off times (t2, t2'). By varying the PRF, the sidebands move back and forth and the average of the sidebands is reduced. Thus, the system locks on the center frequency rather than the sidebands. The PRF can be varied between predetermined sequences of PRFs or can be varied randomly.

Figure 23:
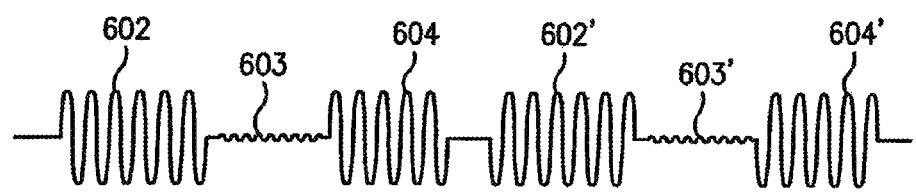
FIG. 23 illustrates phase dithering.

In another aspect, the coupling loop can switch between an energizing mode and a coupling mode. This switching can create transient signals, which can cause a false lock to occur. In one aspect, phase dithering is one method that can be used to reduce the switching transients. As shown in FIG. 23, the system receives a switching transient 603 between the end of the energizing signal 602 and the beginning of the coupled signal 604. To minimize the transient, the phase of the energizing signal may be randomly changed. However, changing the phase of the energizing signal requires that the system redefine zero phase for the interrogation system. To redefine zero phase for the interrogation system, the phase of DDS2 is changed to match the change in phase of the energizing signal. Thus, the phase of the energizing signal 602' and the coupled signal 604' are changed, but the phase of the transient signal 603' is not. As the system changes phase, the average of the transient signal is reduced.

Optionally, changing the resonant frequency of the antenna as it is switched from energizing mode to coupling mode also helps to eliminate the switching transients. The coupled signal appears very quickly after the on period of the energizing signal and dissipates very quickly. In one embodiment, the invention operates in a low power environment with a passive pressure sensor so that the magnitude of the coupled signal is small. In one exemplary aspect, the coupling loop can be tuned to a resonant frequency that is based upon the pressure sensor parameters. Changing the capacitors or capacitor network that is connected to the coupling loop changes the resonant frequency of the antenna. In one aspect, the resonant frequency can be changed from approximately 1/10% to 2% between energizing mode and coupled mode. Additionally, in some aspect, the coupling loop is untuned.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A ventricular shunt system comprising:
    a catheter assembly comprising:
        a valve having an inlet port and an outlet port, the valve configured to control a rate of fluid flow between the inlet port and the outlet port;
        a ventricular catheter having a distal end and a proximal end, the proximal end of the ventricular catheter being coupled to the inlet port of the valve;
        a drainage catheter having a distal end and a proximal end, the proximal end of the drainage catheter being coupled to the outlet port of the valve;
        at least one pressure sensor mountable on a portion of the catheter assembly comprising a passive electrical resonant circuit that is configured to be selectively electromagnetically coupled to an ex-vivo source of radio frequency (RF) energy; wherein the passive electrical resonant circuit is variable in response to the pressure in a patient's ventricle, wherein each passive electrical resonant circuit, in response to the electromagnetic coupling, is configured to generate an output signal characterized by a frequency that is dependent upon urged movement of a portion of the passive electrical resonant circuit and is indicative of pressure in the patient's ventricle, wherein the passive electrical resonant circuit of the at least one pressure sensor comprises an inductance-capacitance (LC) resonant circuit that comprises an inductor operably coupled to a capacitor; and
    a sealed reservoir having a distal end positionable proximate the distal end of the ventricular catheter, the sealed reservoir configured to contain a non-compressible fluid, wherein a portion of the distal end of the reservoir is pliable,
    wherein the at least one pressure sensor is mountable to detect the pressure of the non-compressible fluid within the sealed reservoir, and wherein the at least one pressure sensor is mounted in a wall of the reservoir.

2. The ventricular shunt system of claim 1, wherein the inductor is a coil inductor.

3. The ventricular shunt system of claim 1, wherein the capacitance of the capacitor is variable in response to the pressure therein the patient's ventricle.

4. The ventricular shunt system of claim 1, wherein the capacitor comprises a first and second spaced capacitor elements, wherein at least one of the spaced capacitor elements are mounted in or on a flexible material, and wherein the respective first and second capacitor elements are movable relative to each other in response to pressure changes applied to the flexible material.

5. The ventricular shunt system of claim 1, wherein the inductor is configured to allow inductance in the passive electrical resonant circuit when the pressure sensor is subjected to a time variable electromagnetic field.

6. The ventricular shunt system of claim 1, wherein the inductance of the LC resonant circuit is between about 5 to about 15 micro-Henry.

7. The ventricular shunt system of claim 1, wherein the resonant frequency of the LC resonant circuit is between about 25 to about 45 MHz.

8. The ventricular shunt system of claim 1, wherein the capacitance of the LC resonant circuit is between about 1 to about 20 pF.

9. The ventricular shunt system of claim 1, wherein at least a portion of each pressure sensor is resiliently flexible.

10. The ventricular shunt system of claim 1, wherein the capacitor of each at least one pressure sensor is electrically coupled to a single inductor.

11. The ventricular shunt system of claim 1, wherein the at least one pressure sensor comprises a plurality of individually addressable pressure sensors, the plurality of individually addressable pressure sensors are mounted within the ventricular catheter in spaced relationship.

12. The ventricular shunt system of claim 11, wherein at least one pressure sensor of the plurality of individually addressable pressure sensors is mounted within the drainage catheter.

13. The ventricular shunt system of claim 1, wherein the at least one pressure sensor comprises a plurality of individually addressable pressure sensors, wherein one pressure sensor of the plurality of individually addressable pressure sensors is mounted within the ventricular catheter adjacent the distal end of the ventricular catheter.

14. The ventricular shunt system of claim 13, wherein a plurality of individually addressable pressure sensors are mounted within the ventricular catheter in spaced relationship.

15. The ventricular shunt system of claim 13, wherein at least one pressure sensor of the plurality of individually addressable pressure sensors is mounted within the drainage catheter.

16. The ventricular shunt system of claim 1, wherein the valve is an adjustable valve configured to allow selective flow rates therebetween the respective inlet and outlet ports of the valve.

17. The ventricular shunt system of claim 1, wherein the passive electrical resonant circuit of the at least one pressure sensor comprises a non-linear element and responds in a non-linear manner to an energizing signal.

18. A ventricular shunt system comprising:
a catheter assembly comprising:
a valve having an inlet port and an outlet port, the valve configured to control a rate of fluid flow between the inlet port and the outlet port;
a ventricular catheter having a distal end and a proximal end, the proximal end of the ventricular catheter being coupled to the inlet port of the valve;
a drainage catheter having a distal end and a proximal end, the proximal end of the drainage catheter being coupled to the outlet port of the valve; and
at least one pressure sensor mountable on a portion of the catheter assembly comprising a passive electrical resonant circuit that is configured to be selectively electromagnetically coupled to an ex-vivo source of radio frequency (RF) energy; wherein the passive electrical resonant circuit is variable in response to the pressure in a patient's ventricle, and wherein each passive electrical resonant circuit, in response to the electromagnetic coupling, is configured to generate an output signal characterized by a frequency that is dependent upon urged movement of a portion of the passive electrical resonant circuit and is indicative of pressure in the patient's ventricle; and
a sealed reservoir having a distal end positionable proximate the distal end of the ventricular catheter, the sealed reservoir configured to contain a non-compressible fluid, wherein a portion of the distal end of the reservoir is pliable,
wherein the at least one pressure sensor is mountable to detect the pressure of the non-compressible fluid within the sealed reservoir, and wherein the at least one pressure sensor is mounted in a wall of the reservoir.

19. The ventricular shunt system of claim 18, wherein the passive electrical resonant circuit of the at least one pressure sensor comprises an inductance-capacitance (LC) resonant circuit that comprises an inductor operably coupled to a capacitor.

20. The ventricular shunt system of claim 19, wherein the capacitance of the capacitor is variable in response to the pressure therein the patient's ventricle.

21. The ventricular shunt system of claim 19, wherein the capacitor comprises a first and second spaced capacitor elements, wherein at least one of the spaced capacitor elements are mounted in or on a flexible material, and wherein the respective first and second capacitor elements are movable relative to each other in response to pressure changes applied to the flexible material.

22. The ventricular shunt system of claim 19, wherein the inductor is configured to allow inductance in the passive electrical resonant circuit when the pressure sensor is subjected to a time variable electromagnetic field.

23. The ventricular shunt system of claim 18, wherein the at least one pressure sensor comprises a plurality of individually addressable pressure sensors, wherein at least one pressure sensor of the plurality of individually addressable pressure sensors are mounted within the ventricular catheter in spaced relationship.

24. The ventricular shunt system of claim 23, wherein at least one pressure sensor of the plurality of individually addressable pressure sensors is mounted within the drainage catheter.

25. The ventricular shunt system of claim 18, wherein the valve is an adjustable valve configured to allow selective flow rates therebetween the respective inlet and outlet ports of the valve.

26. The ventricular shunt system of claim 19, wherein the passive electrical resonant circuit of the at least one pressure sensor comprises a non-linear element and responds in a non-linear manner to an energizing signal.

27. A ventricular shunt system comprising:
a catheter assembly comprising:
a valve having an inlet port and an outlet port, the valve configured to control a rate of fluid flow between the inlet port and the outlet port;
a ventricular catheter having a distal end and a proximal end, the proximal end of the ventricular catheter being coupled to the inlet port of the valve;
a drainage catheter having a distal end and a proximal end, the proximal end of the drainage catheter being coupled to the outlet port of the valve; and
a plurality of individually addressable pressure sensors mountable on a portion of the catheter assembly, each pressure sensor comprising a passive electrical resonant circuit that is configured to be selectively electromagnetically coupled to an ex-vivo source of radio frequency (RF) energy; wherein the passive electrical resonant circuit is variable in response to the pressure in a patient's ventricle, wherein each passive electrical resonant circuit, in response to the electromagnetic coupling, is configured to generate an output signal characterized by a frequency that is dependent upon urged movement of a portion of the passive electrical resonant circuit and is indicative of pressure in the patient's ventricle, wherein the passive electrical resonant circuit of the at least one pressure sensor comprises an inductance-capacitance (LC) resonant circuit that comprises an inductor operably coupled to a capacitor, wherein one pressure sensor of the plurality of individually addressable pressure sensors is mounted within the ventricular catheter adjacent the distal end of the ventricular catheter, and wherein at least one pressure sensor of the plurality of individually addressable pressure sensors is mounted within the drainage catheter.

28. The ventricular shunt system of claim 27, wherein the capacitance of the capacitor is variable in response to the pressure therein the patient's ventricle.

29. The ventricular shunt system of claim 27, wherein the capacitor comprises a first and second spaced capacitor elements, wherein at least one of the spaced capacitor elements are mounted in or on a flexible material, and wherein the respective first and second capacitor elements are movable relative to each other in response to pressure changes applied to the flexible material.

30. The ventricular shunt system of claim 27, wherein the inductor is configured to allow inductance in the passive electrical resonant circuit when the pressure sensor is subjected to a time variable electromagnetic field.

31. The ventricular shunt system of claim 27, wherein the valve is an adjustable valve configured to allow selective flow rates therebetween the respective inlet and outlet ports of the valve.

32. The ventricular shunt system of claim 27, wherein the passive electrical resonant circuit of the at least one pressure sensor comprises a non-linear element and responds in a non-linear manner to an energizing signal.

33. The ventricular shunt system of claim 27, wherein the plurality of individually addressable pressure sensors are mounted within the ventricular catheter in spaced relationship.

34. A ventricular shunt system comprising:
a catheter assembly comprising:
  a valve having an inlet port and an outlet port, the valve configured to control a rate of fluid flow between the inlet port and the outlet port;
  a ventricular catheter having a distal end and a proximal end, the proximal end of the ventricular catheter being coupled to the inlet port of the valve;
  a drainage catheter having a distal end and a proximal end, the proximal end of the drainage catheter being coupled to the outlet port of the valve; and
at least one pressure sensor mountable on a portion of the catheter assembly comprising a passive electrical resonant circuit that is configured to be selectively electromagnetically coupled to an ex-vivo source of radio frequency (RF) energy; wherein the passive electrical resonant circuit is variable in response to the pressure in a patient's ventricle, and wherein each passive electrical resonant circuit, in response to the electromagnetic coupling, is configured to generate an output signal characterized by a frequency that is dependent upon urged movement of a portion of the passive electrical resonant circuit and is indicative of pressure in the patient's ventricle,
wherein one pressure sensor of the plurality of individually addressable pressure sensors is mounted within the ventricular catheter adjacent the distal end of the ventricular catheter, and wherein at least one pressure sensor of the plurality of individually addressable pressure sensors is mounted within the drainage catheter.

35. The ventricular shunt system of claim 34, wherein the passive electrical resonant circuit of the at least one pressure sensor comprises an inductance-capacitance (LC) resonant circuit that comprises an inductor operably coupled to a capacitor.

36. The ventricular shunt system of claim 35, wherein the capacitance of the capacitor is variable in response to the pressure therein the patient's ventricle.

37. The ventricular shunt system of claim 35, wherein the capacitor comprises a first and second spaced capacitor elements, wherein at least one of the spaced capacitor elements are mounted in or on a flexible material, and wherein the respective first and second capacitor elements are movable relative to each other in response to pressure changes applied to the flexible material.

38. The ventricular shunt system of claim 35, wherein the inductor is configured to allow inductance in the passive electrical resonant circuit when the pressure sensor is subjected to a time variable electromagnetic field.

39. The ventricular shunt system of claim 34, wherein the at least one pressure sensor comprises a plurality of individually addressable pressure sensors, wherein at least one pressure sensor of the plurality of individually addressable pressure sensors are mounted within the ventricular catheter in spaced relationship.

40. The ventricular shunt system of claim 35, wherein the passive electrical resonant circuit of the at least one pressure sensor comprises a non-linear element and responds in a non-linear manner to an energizing signal.

41. The ventricular shunt system of claim 34, wherein the plurality of individually addressable pressure sensors are mounted within the ventricular catheter in spaced relationship.

* * * * *